US012661012B2

(12) United States Patent
Panchawagh et al.

(10) Patent No.: US 12,661,012 B2
(45) Date of Patent: Jun. 23, 2026

(54) PHOTOACOUSTIC SENSOR WITH LIGHT-STEERING SYSTEM

(71) Applicant: QUALCOMM Incorporated, San Diego, CA (US)

(72) Inventors: Hrishikesh Vijaykumar Panchawagh, Cupertino, CA (US); Ali Lopez, Dublin, CA (US); Sumit Agrawal, Sunnyvale, CA (US); Bernard Herrera Soukup, Sunnyvale, CA (US); Nicholas Buchan, San Jose, CA (US); Camilo Perez Saaibi, Dublin, CA (US); Legardo Reyes, Fremont, CA (US); Kostadin Dimitrov Djordjev, Los Gatos, CA (US)

(73) Assignee: QUALCOMM Incorporated, San Diego, CA (US)

( * ) Notice: Subject to any disclaimer, the term of this patent is extended or adjusted under 35 U.S.C. 154(b) by 121 days.

(21) Appl. No.: 18/461,423

(22) Filed: Sep. 5, 2023

(65) Prior Publication Data

US 2025/0072764 A1     Mar. 6, 2025

(51) Int. Cl.
*A61B 5/00*     (2006.01)
*A61B 5/02*     (2006.01)
*A61B 5/021*    (2006.01)

(52) U.S. Cl.
CPC ........ *A61B 5/0095* (2013.01); *A61B 5/02007* (2013.01); *A61B 5/021* (2013.01); *A61B 5/6802* (2013.01); *A61B 5/721* (2013.01)

(58) Field of Classification Search
CPC .............. A61B 5/0095; A61B 5/02007; A61B 5/021; A61B 5/6802; A61B 5/721; A61B 5/1075; A61B 5/489
See application file for complete search history.

(56) References Cited

U.S. PATENT DOCUMENTS

2007/0249916 A1* 10/2007 Pesach ................ A61B 5/1455
                                                          600/316
2009/0149761 A1*  6/2009 Zou ...................... A61B 5/0095
                                                          600/476

(Continued)

FOREIGN PATENT DOCUMENTS

CN        208808486 U    5/2019
CN        110742622 A    2/2020

(Continued)

OTHER PUBLICATIONS

International Search Report and Written Opinion—PCT/US2024/045219—ISA/EPO—Dec. 2, 2024.

*Primary Examiner* — Bo Joseph Peng
(74) *Attorney, Agent, or Firm* — Weaver Austin Villeneuve & Sampson LLP

(57)     ABSTRACT

Some disclosed examples involve controlling a light-steering system to direct light emitted by at least a first light source of a light source system to a first plurality of areas of a target object, wherein controlling the light-steering system involves controlling one or more adjustable micromirrors, one or more adjustable lenses, one or more adjustable diffraction gratings, or combinations thereof. Some examples involve receiving ultrasonic receiver signals from an ultrasonic receiver system corresponding to photoacoustic responses of the target object to light provided the light source system to each area of the first plurality of areas and determining a selected area of the target object from which additional ultrasonic receiver signals will be obtained, wherein determining the selected area involves detecting a blood vessel within the target object. Some examples involve controlling the light source system to obtain additional ultrasonic receiver signals from the selected area.

24 Claims, 15 Drawing Sheets

(56)     References Cited

U.S. PATENT DOCUMENTS

| | | | |
|---|---|---|---|
| 2014/0169527 A1 | 6/2014 | Luo et al. | |
| 2017/0215739 A1* | 8/2017 | Miyasato | A61B 5/14542 |
| 2017/0325698 A1* | 11/2017 | Allec | A61B 5/721 |
| 2018/0192993 A1 | 7/2018 | Goergen et al. | |
| 2019/0377962 A1 | 12/2019 | Kitchens et al. | |
| 2021/0015991 A1* | 1/2021 | Drori | A61B 5/02007 |

FOREIGN PATENT DOCUMENTS

| | | | | |
|---|---|---|---|---|
| CN | 109363644 B | 4/2021 | | |
| WO | WO-2022005863 A1 * | 1/2022 | | A61B 5/0095 |

* cited by examiner

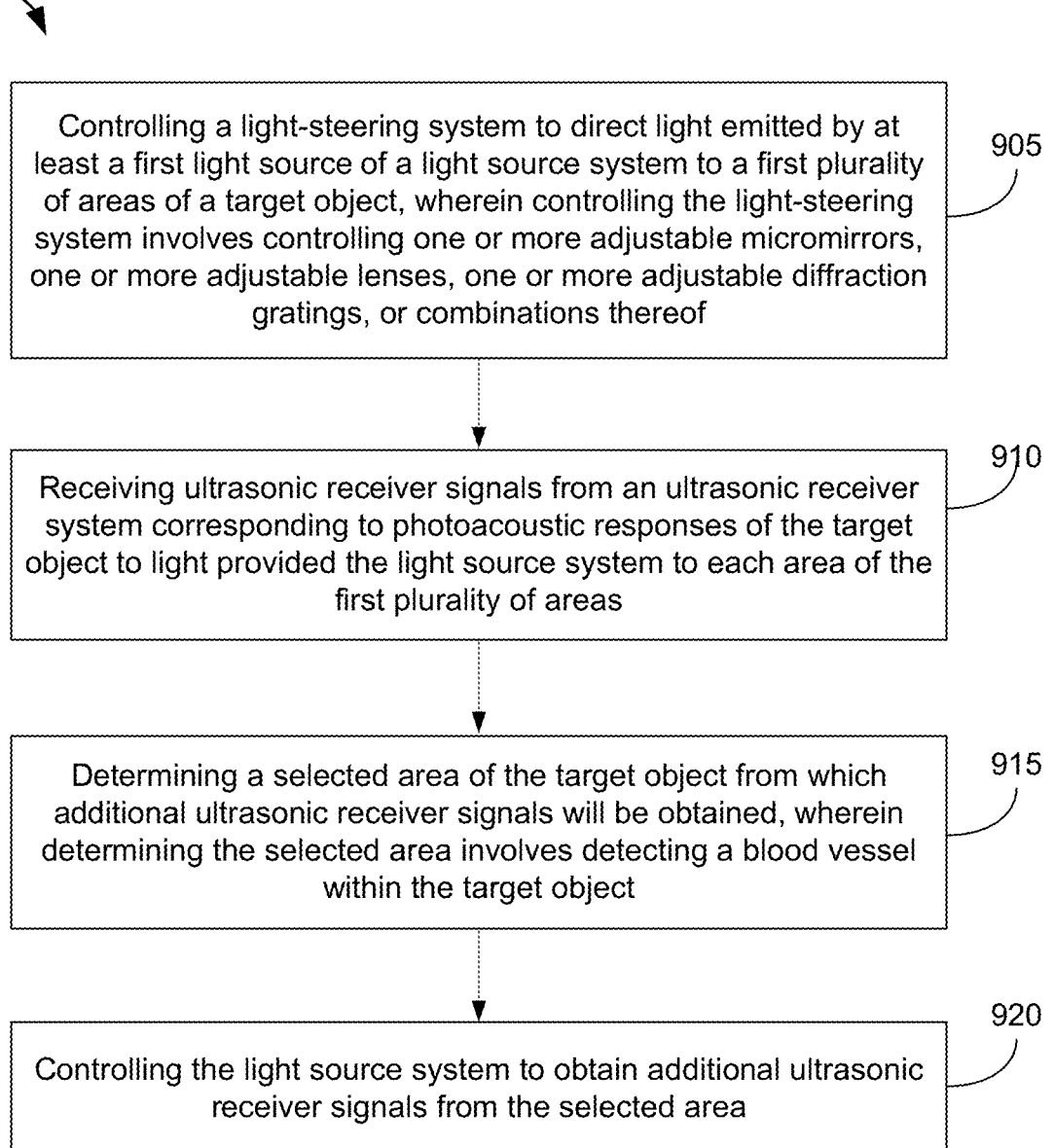

905

Controlling a light-steering system to direct light emitted by at least a first light source of a light source system to a first plurality of areas of a target object, wherein controlling the light-steering system involves controlling one or more adjustable micromirrors, one or more adjustable lenses, one or more adjustable diffraction gratings, or combinations thereof

910

Receiving ultrasonic receiver signals from an ultrasonic receiver system corresponding to photoacoustic responses of the target object to light provided the light source system to each area of the first plurality of areas

915

Determining a selected area of the target object from which additional ultrasonic receiver signals will be obtained, wherein determining the selected area involves detecting a blood vessel within the target object

920

Controlling the light source system to obtain additional ultrasonic receiver signals from the selected area

*Figure 9*

PHOTOACOUSTIC SENSOR WITH LIGHT-STEERING SYSTEM

TECHNICAL FIELD

This disclosure relates generally to photoacoustic devices and more specifically to light source systems for photoacoustic devices.

DESCRIPTION OF RELATED TECHNOLOGY

A variety of different sensing technologies and algorithms are being implemented in devices for various biometric and biomedical applications, including health and wellness monitoring. This push is partly a result of the limitations in the usability of traditional measuring devices for continuous, noninvasive and ambulatory monitoring. Some such devices are, or include, photoacoustic devices. Although some previously-deployed photoacoustic devices and systems can provide acceptable results, improved photoacoustic devices and systems would be desirable.

SUMMARY

The systems, methods and devices of this disclosure each have several aspects, no single one of which is solely responsible for the desirable attributes disclosed herein.

One innovative aspect of the subject matter described in this disclosure can be implemented in an apparatus. The apparatus may include a light source system, a control system and a receiver system. The light source system may include a light-steering system having one or more light-steering devices configured to direct light emitted by one or more light sources of the light source system to a plurality of areas of a target object. The receiver system may be, or may include, an ultrasonic receiver system configured to receive ultrasonic waves generated by the target object responsive to the light from the light source system and to generate ultrasonic receiver signals based, at least in part, on the ultrasonic waves generated by the target object. In some implementations, a mobile device (such as a wearable device, a cellular telephone, etc.) may be, or may include, at least part of the apparatus.

In some implementations, the apparatus may include a control system. The control system may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. The control system may be configured to receive ultrasonic receiver signals from the ultrasonic receiver system, the ultrasonic receiver signals corresponding to each area of the first plurality of areas of the target object. The control system may be configured to determine a selected area of the target object corresponding to an area from which additional ultrasonic receiver signals will be obtained. Determining the selected area may involve detecting a blood vessel within the target object. The control system may be configured to control the light source system to obtain the additional ultrasonic receiver signals from the selected area.

In some examples, determining the selected area may involve estimating a signal-to-noise ratio (SNR) of ultrasonic receiver signals corresponding to at least a portion of the blood vessel. In some examples, determining the selected area may involve selecting an area corresponding to a highest SNR. In some examples, determining the selected area may involve selecting an area corresponding to a greatest estimated distance between a first blood vessel wall and a second blood vessel wall.

In some examples, the light-steering system may include one or more adjustable micromirrors, one or more adjustable lenses, one or more adjustable diffraction gratings, or combinations thereof. According to some examples, the light-steering system may include a second light-steering device configured to direct light emitted by a second light source of the light source system to a second plurality of areas of the target object. In some examples, the first light-steering device may be configured to direct light emitted by a second light source of the light source system to a second plurality of areas of the target object.

According to some examples, the light-steering system may include a plurality of light guides. In some examples, the light-steering system may be configured to direct light emitted by at least the first light source to each light guide of the plurality of light guides. According to some examples, the ultrasonic receiver system may include a plurality of receiver portions. In some such examples, each receiver portion may correspond to one light guide of the plurality of light guides. According to some examples, each light guide of the plurality of light guides may be configured to direct a first portion of received light along an axis of the light guide and to direct a second portion of the received light towards the target object.

Other innovative aspects of the subject matter described in this disclosure can be implemented in a method. The method may involve controlling a light-steering system to direct light emitted by at least a first light source of a light source system to a first plurality of areas of a target object. Controlling the light-steering system may involve controlling one or more adjustable micromirrors, one or more adjustable lenses, one or more adjustable diffraction gratings, or combinations thereof. The method may involve receiving ultrasonic receiver signals from an ultrasonic receiver system, the ultrasonic receiver signals corresponding to photoacoustic responses of the target object to light provided the light source system to each area of the first plurality of areas. The method may involve determining a selected area of the target object corresponding to an area from which additional ultrasonic receiver signals will be obtained. In some examples, determining the selected area may involve detecting a blood vessel within the target object. The method may involve controlling the light source system to obtain the additional ultrasonic receiver signals from the selected area.

In some examples, determining the selected area may involve estimating a signal-to-noise ratio (SNR) of ultrasonic receiver signals corresponding to at least a portion of the blood vessel. According to some examples, determining the selected area may involve selecting an area corresponding to a highest SNR. In some examples, determining the selected area may involve selecting an area corresponding to a greatest estimated distance between a first blood vessel wall and a second blood vessel wall. According to some examples, controlling the light-steering system may involve directing light emitted by at least the first light source to each light guide of a plurality of light guides.

Some or all of the methods described herein may be performed by one or more devices according to instructions (e.g., software) stored on non-transitory media. Such non-transitory media may include memory devices such as those described herein, including but not limited to random access memory (RAM) devices, read-only memory (ROM)

devices, etc. Accordingly, some innovative aspects of the subject matter described in this disclosure can be implemented in one or more non-transitory media having software stored thereon. The software may include instructions for controlling one or more devices to perform one or more disclosed methods.

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale.

BRIEF DESCRIPTION OF THE DRAWINGS

FIG. 9 is a flow diagram that shows examples of some disclosed operations.

Like reference numbers and designations in the various drawings indicate like elements.

DETAILED DESCRIPTION

Figure 1A:
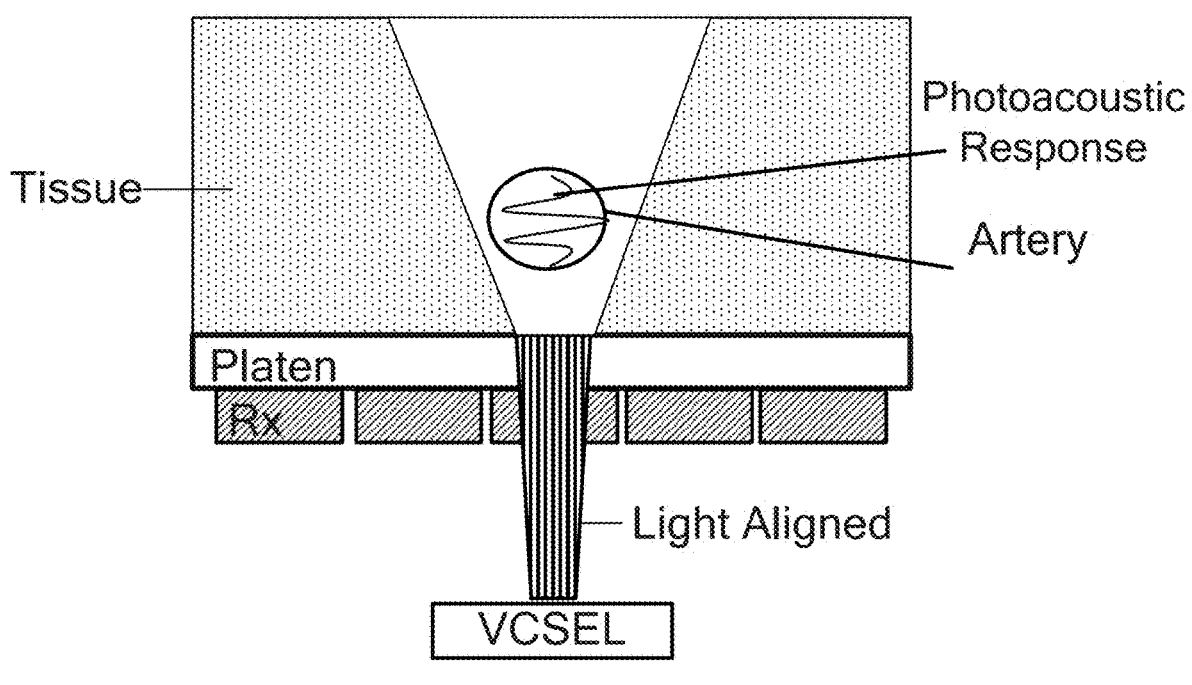
FIG. 1A shows an example of a light source that is properly aligned with an artery.

The following description is directed to certain implementations for the purposes of describing various aspects of this disclosure. However, a person having ordinary skill in the art will readily recognize that the teachings herein can be applied in a multitude of different ways. Some of the concepts and examples provided in this disclosure are especially applicable to blood pressure monitoring applications. However, some implementations also may be applicable to other types of biological sensing applications, as well as to other fluid flow systems. The described implementations may be implemented in any device, apparatus, or system that includes an apparatus as disclosed herein. In addition, it is contemplated that the described implementations may be included in or associated with a variety of electronic devices such as, but not limited to: mobile telephones, multimedia Internet enabled cellular telephones, mobile television receivers, wireless devices, smartphones, smart cards, wearable devices such as bracelets, armbands, wristbands, rings, headbands, patches, etc., Bluetooth® devices, personal data assistants (PDAs), wireless electronic mail receivers, handheld or portable computers, netbooks, notebooks, smartbooks, tablets, printers, copiers, scanners, facsimile devices, global positioning system (GPS) receivers/navigators, cameras, digital media players, game consoles, wrist watches, clocks, calculators, television monitors, flat panel displays, electronic reading devices (e.g., e-readers), mobile health devices, computer monitors, auto displays (including odometer and speedometer displays, etc.), cockpit controls and/or displays, camera view displays (such as the display of a rear view camera in a vehicle), architectural structures, microwaves, refrigerators, stereo systems, cassette recorders or players, DVD players, CD players, VCRs, radios, portable memory chips, washers, dryers, washer/dryers, parking meters, automobile doors, autonomous or semi-autonomous vehicles, drones, Internet of Things (IoT) devices, etc. Thus, the teachings are not intended to be limited to the specific implementations depicted and described with reference to the drawings; rather, the teachings have wide applicability as will be readily apparent to persons having ordinary skill in the art.

Non-invasive health monitoring devices, such as photoacoustic plethysmography (PAPG)-capable devices, have various potential advantages over more invasive health monitoring devices such as cuff-based or catheter-based blood pressure measurement devices. However, it has proven to be difficult to design satisfactory PAPG-capable devices. One challenge is that the signal-to-noise ratio (SNR) for signals of interest, such as signals corresponding to ultrasound caused by the photoacoustic response of arterial walls, is low. For example, the signals corresponding to arterial walls are generally significantly lower in amplitude than signals corresponding to the photoacoustic response of skin.

Figure 1B:
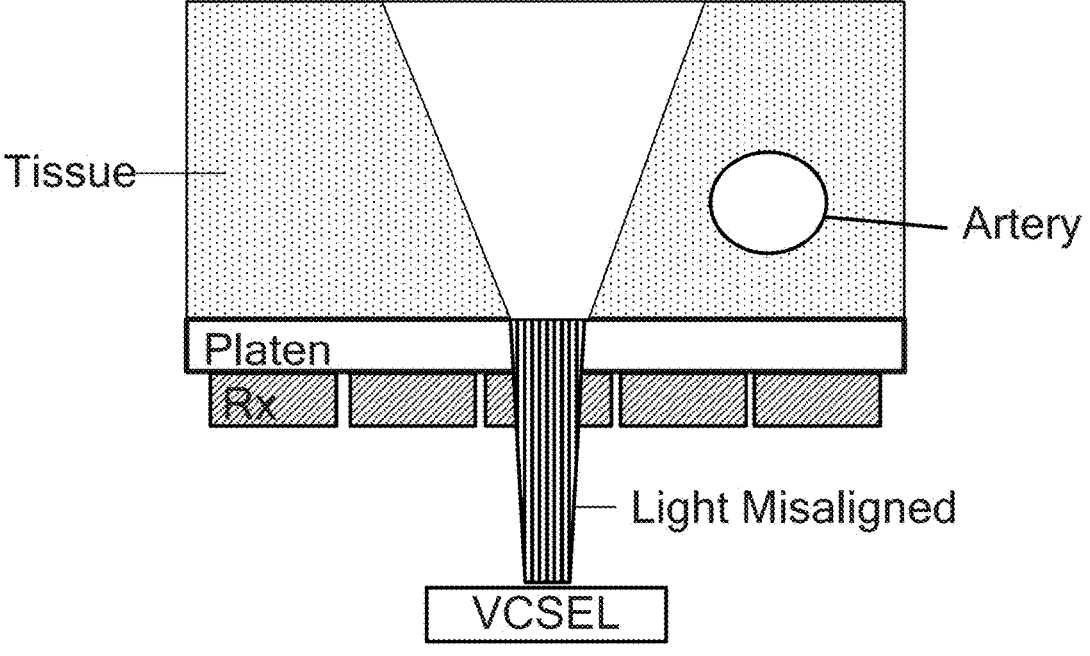
FIG. 1B shows an example of a light source that is not properly aligned with an artery.

Another challenge is that the orientation of the same artery may vary from user to user and within the body of the same user. These variations in arterial orientation can make it challenging to direct light to an artery. One example of a properly-illuminated artery is shown in FIG. 1A, which shows a waveform within the artery representing a photoacoustic response to the light provided by a single vertical-cavity surface-emitting laser (VCSEL). FIG. 1B shows an example in which the light from the light source is misaligned with the artery. Simulations show that even a 1.5 millimeter (mm) misalignment of the light can cause significant degradation of the resulting photoacoustic signal. One solution to possible misalignment would be to use an array of suitable light sources. However, such implementations would require high input power and/or switching capability of each light source in the array. Laser light sources, such as vertical-cavity surface-emitting lasers (VCSELs) and edge emitting lasers (EELs), require high (e.g., 10-25 ampere) current pulses, for example at intervals of 200 nanoseconds (ns) or less. Therefore, PAPG-capable devices having a suitable array of light sources could be expensive and complex, and could consume a lot of power.

Some disclosed devices include a light source system, a control system and a receiver system. The light source system may include a light-steering system having one or more light-steering devices configured to direct light emitted by one or more light sources of the light source system to a plurality of areas of a target object. The light-steering system may, for example, include one or more rotatable micromirrors, such as one or more microelectromechanical (MEMS) tortional micromirrors. Alternatively, or additionally, the light-steering system may include one or more movable lenses, one or more movable diffraction gratings, etc. According to some examples, the control system may be configured to receive ultrasonic receiver signals from the receiver system corresponding to each area of a plurality of illuminated areas of the target object. In some examples, the control system may be configured to determine a selected area of the target object from which additional ultrasonic receiver signals will be obtained. According to some such examples, determining the selected area may involve detecting a blood vessel within the target object. In some examples, the control system may be configured to control the light source system to obtain additional ultrasonic receiver signals from the selected area.

Particular implementations of the subject matter described in this disclosure can be implemented to realize one or more of the following potential advantages. Various disclosed configurations include PAPG-capable devices that can direct light to multiple areas of the target object, while including only one or two light sources. Accordingly, the number of illuminated areas of the target object may be greater (for example 5×, 10×, 15×, 20×, etc.) than the number of light sources. Accordingly, PAPG-capable devices having a light-steering system may be less expensive, may be less complex and may consume less power than PAPG-capable devices having an array of light sources, with each light source corresponding to one of multiple illuminated areas of the target object.

Figure 1C:
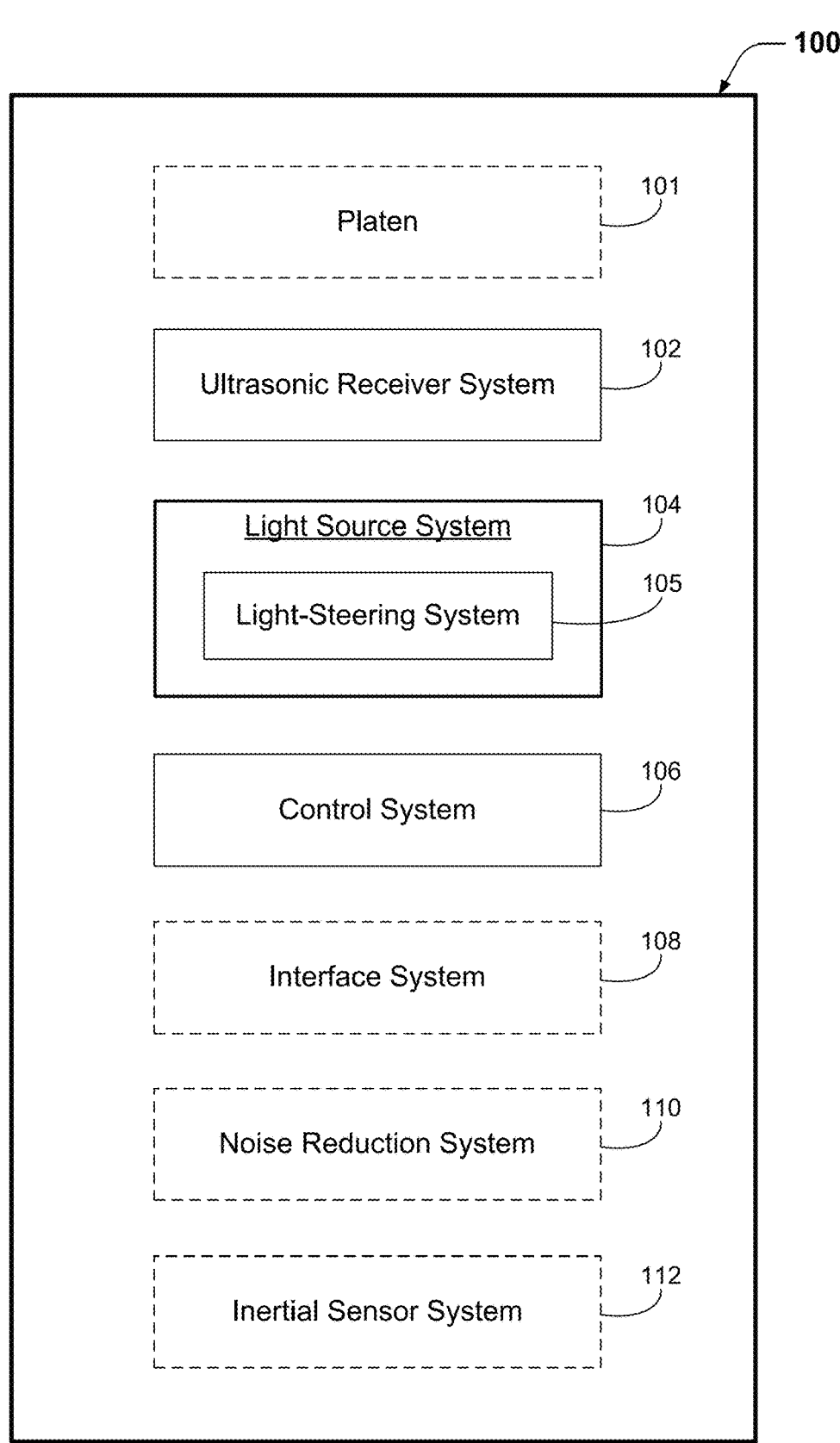
FIG. 1C is a block diagram that shows example components of an apparatus according to some disclosed implementations.

FIG. 1C is a block diagram that shows example components of an apparatus according to some disclosed implementations. In this example, the apparatus 100 includes an ultrasonic receiver system 102, a light source system 104 and a control system 106. Some implementations of the apparatus 100 may include a platen 101, an interface system 108, a noise reduction system 110, an inertial sensor system 112, or combinations thereof. As with other disclosed implementations, in some alternative implementations the apparatus 100 may include more components, fewer components or different components.

According to some examples, the platen 101 (if present) may include one or more anti-reflective layers. In some examples, one or more anti-reflective layers may reside on, or proximate, one or more outer surfaces of the platen 101.

In some examples, at least a portion of the outer surface of the platen 101 (if present) may have an acoustic impedance that is configured to approximate an acoustic impedance of human skin. The portion of the outer surface of the platen 101 may, for example, be a portion that is configured to receive a target object, such as a human digit. (As used herein, the terms "finger" and "digit" may be used interchangeably, such that a thumb is one example of a finger.) A typical range of acoustic impedances for human skin is 1.53-1.680 MRayls. In some examples, at least an outer surface of the platen 101 may have an acoustic impedance that is in the range of 1.4-1.8 MRayls, or in the range of 1.5-1.7 MRayls.

Alternatively, or additionally, in some examples at least an outer surface of the platen 101 (if present) may be configured to conform to a surface of human skin. In some such examples, at least an outer surface of the platen 101 may have material properties like those of putty or chewing gum.

In some examples, at least a portion of the platen 101 (if present) may have an acoustic impedance that is configured to approximate an acoustic impedance of one or more receiver elements of the ultrasonic receiver system 102. According to some examples, a layer residing between the platen 101 and one or more receiver elements may have an acoustic impedance that is configured to approximate an acoustic impedance of the one or more receiver elements. Alternatively, or additionally, in some examples a layer residing between the platen 101 and one or more receiver elements may have an acoustic impedance that is in an acoustic impedance range between an acoustic impedance of the platen and an acoustic impedance of the one or more receiver elements.

According to some examples, the platen 101 (if present) may include one or more light guides. In some such examples, each of the one or more light guides may be configured to direct a first portion of received light along an axis of the light guide. In some such examples, each of the one or more light guides may include one or more light-extracting elements. According to some such examples, each of the one or more light guides may be configured to direct a second portion of the received light towards the target object.

Various examples and configurations of ultrasonic receiver systems 102 may be used in implementations disclosed herein. Some examples are described in more detail below. According to some examples, part or all of the ultrasonic receiver system 102—such as the electrodes, piezoelectric material, or both—may include transparent material. In some examples, the ultrasonic receiver system 102 may include an array of ultrasonic receiver elements, such as a linear array or a two-dimensional array. However, other examples may not include an array of ultrasonic receiver elements. In some examples, the ultrasonic receiver system 102 may include an array of electrodes arranged on a piezoelectric receiver layer, such as a layer of PVDF polymer, a layer of PVDF-TrFE copolymer, or a layer of piezoelectric composite material. In some implementations, other piezoelectric materials may be used in the piezoelectric layer, such as aluminum nitride (AlN) or lead zirconate titanate (PZT). The ultrasonic receiver system 102 may, in some examples, include an array of ultrasonic transducer elements, such as an array of piezoelectric micromachined ultrasonic transducers (PMUTs), an array of capacitive micromachined ultrasonic transducers (CMUTs), etc. In some such examples, a piezoelectric receiver layer, PMUT elements in a single-layer array of PMUTs, or CMUT elements in a single-layer array of CMUTs, may be used as ultrasonic transmitters as well as ultrasonic receivers. According to some examples, the ultrasonic receiver system 102 may be, or may include, an ultrasonic receiver array. In some examples, the apparatus 100 may include one or more separate ultrasonic transmitter elements. In some such examples, the ultrasonic transmitter(s) may include an ultrasonic plane-wave generator.

According to some implementations, the light source system 104 may include one or more light-emitting diodes (LEDs). In some implementations, the light source system 104 may include one or more laser diodes. According to some implementations, the light source system 104 may include one or more vertical-cavity surface-emitting lasers (VCSELs). In some implementations, the light source system 104 may include one or more edge-emitting lasers (EELs). In some implementations, the light source system may include one or more neodymium-doped yttrium aluminum garnet (Nd:YAG) lasers. The light source system 104 may, in some examples, include an array of light-emitting elements, such as an array of LEDs, an array of laser diodes, an array of VCSELs, an array of edge-emitting lasers, or combinations thereof. However, it can be advantageous to limit the number of light-emitting elements to a relatively small number, such as 1 light-emitting elements, 2 light-emitting elements, 3 light-emitting elements, etc.

In this example, the light source system 104 includes a light-steering system 105. In some examples, light-steering system 105 may include one or more light-steering devices configured to direct light emitted by one or more light sources of the light source system 104 to a plurality of areas of the target object. According to some examples, the one or more light-steering devices may include one or more movable micromirrors, such as one or more movable MEMS micromirrors. Alternatively, or additionally, the one or more light-steering devices may include one or more movable lenses, one or more movable diffraction gratings, etc. In some examples, the light-steering system 105 may be configured to direct light emitted by one or more light sources of the light source system through transparent portions of the ultrasonic receiver system 102 to a plurality of areas of the target object.

In some examples, a single light-steering device may be configured to direct light emitted by two or more light sources of the light source system to a plurality of areas of the target object. According to some such examples, at least one of the two or more light sources may have a different peak frequency than that of the other light source(s). In some examples, a light-steering device may be configured to direct first light emitted by a first light source to a first plurality of areas and configured to direct second light emitted by a second light source to a second plurality of areas. According to some such examples, the light-steering device may be configured to direct the first light to the first plurality of areas at a first time and configured to direct the second light to the second plurality of areas at a second time that is different from the first time. In some such examples, the first light may have a peak amplitude at a first wavelength and the second light may have a peak amplitude at a second wavelength. In some alternative examples, a first light-steering device may be configured to direct first light emitted by a first light source to a first plurality of areas and a second light-steering device may be configured to direct second light emitted by a second light source to a second plurality of areas.

According to some examples, the one or more light-steering devices may be configured to direct light emitted by at least the first light source to each light guide of a plurality of light guides. The platen 101 may, in some examples, include the plurality of light guides. According to some examples, the ultrasonic receiver system 102 may include a plurality of receiver portions. In some such examples, each receiver portion may correspond to one light guide of the plurality of light guides.

The light source system 104 may, in some examples, be configured to transmit light in one or more wavelength ranges. In some examples, the light source system 104 may configured for transmitting light in a wavelength range of 500 to 600 nanometers. According to some examples, the light source system 104 may configured for transmitting light in a wavelength range of 800 to 950 nanometers.

The light source system 104 may include various types of drive circuitry, depending on the particular implementation. In some disclosed implementations, the light source system 104 may include at least one multi-junction laser diode, which may produce less noise than single-junction laser diodes. In some examples, the light source system 104 may include a drive circuit (also referred to herein as drive circuitry) configured to cause the light source system to emit pulses of light at pulse widths in a range from 3 nanoseconds to 1000 nanoseconds. According to some examples, the light source system 104 may include a drive circuit configured to cause the light source system to emit pulses of light at pulse repetition frequencies in a range from 1 kilohertz to 100 kilohertz.

In some examples, the light source system 104 may include a light source system surface having a normal that is parallel, or substantially parallel, to the first axis. In some such examples, a light source of the light source system may reside on, or proximate, the light source system surface.

In some implementations, the light source system 104 may be configured for emitting various wavelengths of light, which may be selectable to trigger acoustic wave emissions primarily from a particular type of material. For example, because the hemoglobin in blood absorbs near-infrared light very strongly, in some implementations the light source system 104 may be configured for emitting one or more wavelengths of light in the near-infrared range, in order to trigger acoustic wave emissions from hemoglobin. However, in some examples the control system 106 may control the wavelength(s) of light emitted by the light source system 104 to preferentially induce acoustic waves in blood vessels, other soft tissue, and/or bones. For example, an infrared (IR) light-emitting diode LED may be selected and a short pulse of IR light emitted to illuminate a portion of a target object and generate acoustic wave emissions that are then detected by the ultrasonic receiver system 102. In another example, an IR LED and a red LED or other color such as green, blue, white or ultraviolet (UV) may be selected and a short pulse of light emitted from each light source in turn with ultrasonic images obtained after light has been emitted from each light source. In other implementations, one or more light sources of different wavelengths may be fired in turn or simultaneously to generate acoustic emissions that may be detected by the ultrasonic receiver. Image data from the ultrasonic receiver that is obtained with light sources of different wavelengths and at different depths (e.g., varying RGDs) into the target object may be combined to determine the location and type of material in the target object. Image contrast may occur as materials in the body generally absorb light at different wavelengths differently. As materials in the body absorb light at a specific wavelength, they may heat differentially and generate acoustic wave emissions with sufficiently short pulses of light having sufficient intensities. Depth contrast may be obtained with light of different wavelengths and/or intensities at each selected wavelength. That is, successive images may be obtained at a fixed RGD (which may correspond with a fixed depth into the target object) with varying light intensities and wavelengths to detect materials and their locations within a target object. For example, hemoglobin, blood glucose or blood oxygen within a blood vessel inside a target object such as a finger may be detected photoacoustically.

According to some implementations, the light source system 104 may be configured for emitting a light pulse with a pulse width less than about 100 nanoseconds. In some implementations, the light pulse may have a pulse width between about 10 nanoseconds and about 500 nanoseconds or more. According to some examples, the light source system may be configured for emitting a plurality of light pulses at a pulse repetition frequency between 10 Hz and 100 kHz. Alternatively, or additionally, in some implementations the light source system 104 may be configured for emitting a plurality of light pulses at a pulse repetition frequency between about 1 MHz and about 100 MHZ. Alternatively, or additionally, in some implementations the light source system 104 may be configured for emitting a plurality of light pulses at a pulse repetition frequency between about 10 Hz and about 1 MHZ. In some examples, the pulse repetition frequency of the light pulses may correspond to an acoustic resonant frequency of the ultrasonic receiver and the substrate. For example, a set of four or more light pulses may be emitted from the light source system 104 at a frequency that corresponds with the resonant frequency of a resonant acoustic cavity in the sensor stack, allowing a build-up of the received ultrasonic waves and a higher resultant signal strength. In some implementations, filtered light or light sources with specific wavelengths for detecting selected materials may be included with the light source system 104. In some implementations, the light source system may contain light sources such as red, green and blue LEDs of a display that may be augmented with light sources of other wavelengths (such as IR and/or UV) and with light sources of higher optical power. For example, high-power laser diodes or electronic flash units (e.g., an LED or xenon flash unit) with or without filters may be used for short-term illumination of the target object.

The control system 106 may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. The control system 106 also may include (and/or be configured for communication with) one or more memory devices, such as one or more random access memory (RAM) devices, read-only memory (ROM) devices, etc. Accordingly, the apparatus 100 may have a memory system that includes one or more memory devices, though the memory system is not shown in FIG. 1C. The control system 106 may be configured for receiving and processing data from the ultrasonic receiver system 102, e.g., as described below. If the apparatus 100 includes an ultrasonic transmitter, the control system 106 may be configured for controlling the ultrasonic transmitter. In some implementations, functionality of the control system 106 may be partitioned between one or more controllers or processors, such as a dedicated sensor controller and an applications processor of a mobile device.

In some examples, the control system 106 may be configured to control the light source system 104 to emit light towards a target object on an outer surface of the platen 101. In some such examples, the control system 106 may be configured to control the light-steering system 105 to direct light emitted by at least a first light source of the light source system 104 to multiple areas of a target object—for example, to 2, 3, 4, 5, 6, 7, 8, 9, 10, 11, 12, 13, 14, 15, 16, 17, 18, 19, 20 or more areas—on, or proximate, an outer surface of the apparatus 100.

According to some such examples, the control system 106 may be configured to receive signals from the ultrasonic receiver system 102 corresponding to each area of the target object that has been illuminated by the light source system 104. The signals may correspond to ultrasonic waves generated by the target object, in each area of the first plurality of areas, responsive to the light from the light source system 104. In some such examples, the control system 106 may be configured to receive signals from each of a plurality of ultrasonic receiver elements in an array of ultrasonic receiver elements of the ultrasonic receiver system 102. According to some examples, the control system 106 may be configured to determine a selected area of the target object from which additional ultrasonic receiver signals will be obtained. In some such examples, determining the selected area may involve detecting a blood vessel within the target object. In some examples, determining the selected area may involve estimating a signal-to-noise ratio (SNR) of ultrasonic receiver signals corresponding to at least a portion of the blood vessel. In some such examples, the control system 106 may be configured to determine the selected area by selecting an area corresponding to the highest SNR.

In some examples, the control system 106 may be configured to apply a receiver-side beamforming process to the ultrasonic receiver signals, to produce a beamformed ultrasonic receiver image. According to some examples, the control system 106 may be configured to detect a blood vessel within the targe object based, at least in part, on the beamformed ultrasonic receiver image. In some such examples, the control system 106 may be configured to estimate one or more blood vessel features based, at least in part, on the beamformed ultrasonic receiver image. In some examples, the control system 106 may be configured to estimate one or more cardiac features based, at least in part, on one or more arterial signals, on the blood vessel features. According to some examples, the cardiac features may be, or may include, blood pressure.

Some implementations of the apparatus 100 may include the interface system 108. In some examples, the interface system 108 may include a wireless interface system. In some implementations, the interface system 108 may include a user interface system, one or more network interfaces, one or more interfaces between the control system 106 and a memory system and/or one or more interfaces between the control system 106 and one or more external device interfaces (e.g., ports or applications processors), or combinations thereof. According to some examples in which the interface system 108 is present and includes a user interface system, the user interface system may include a microphone system, a loudspeaker system, a haptic feedback system, a voice command system, one or more displays, or combinations thereof. According to some examples, the interface system 108 may include a touch sensor system, a gesture sensor system, or a combination thereof. The touch sensor system (if present) may be, or may include, a resistive touch sensor system, a surface capacitive touch sensor system, a projected capacitive touch sensor system, a surface acoustic wave touch sensor system, an infrared touch sensor system, any other suitable type of touch sensor system, or combinations thereof.

In some examples, the interface system 108 may include, a force sensor system. The force sensor system (if present) may be, or may include, a piezo-resistive sensor, a capacitive sensor, a thin film sensor (for example, a polymer-based thin film sensor), another type of suitable force sensor, or combinations thereof. If the force sensor system includes a piezo-resistive sensor, the piezo-resistive sensor may include silicon, metal, polysilicon, glass, or combinations thereof. An ultrasonic fingerprint sensor and a force sensor system may, in some implementations, be mechanically coupled. In some such examples, the force sensor system may be integrated into circuitry of the ultrasonic fingerprint sensor. In some examples, the interface system 108 may include an optical sensor system, one or more cameras, or a combination thereof.

According to some examples, the apparatus 100 may include a noise reduction system 110. For example, the noise reduction system 110 may include one or more mirrors that are configured to reflect light from the light source system 104 away from the ultrasonic receiver system 102. In some implementations, the noise reduction system 110 may include one or more sound-absorbing layers, acoustic isolation material, light-absorbing material, light-reflecting material, or combinations thereof. In some examples, the noise reduction system 110 may include acoustic isolation material, which may reside between the light source system 104 and at least a portion of the ultrasonic receiver system 102, on at least a portion of the ultrasonic receiver system 102, or combinations thereof. In some examples, the noise reduction system 110 may include one or more electromagnetically shielded transmission wires. In some such examples, the one or more electromagnetically shielded transmission wires may be configured to reduce electromagnetic interference from circuitry of the light source system 104, receiver system circuitry, or combinations thereof, that is received by the ultrasonic receiver system 102. In some examples, the one or more electromagnetically shielded transmission wires, sound-absorbing layers, acoustic isolation material, light-absorbing material, light-reflecting material, or combinations thereof may be components of the ultrasonic receiver system 102, the light source system 104, or both. Despite the fact that the ultrasonic receiver system 102, the light source system 104 and the noise reduction system 110 are shown in FIG. 1C as being separate elements, such components may nonetheless be regarded as elements of the noise reduction system 110.

According to some examples, the apparatus 100 may include an inertial sensor system 112. In some such examples, the inertial sensor system 112 may include one or more gyroscopes, one or more accelerometers, or combinations thereof. The one or more accelerometers are examples of what may be referred to herein as "motion detectors." In some implementations, the control system 106 may be configured to receive inertial sensor data from the inertial sensor system 112 and to control the light-steering system 105 based, at least in part, on the inertial sensor data. For example, the control system 106 may be configured to determine whether the inertial sensor data indicates motion of the apparatus 100 that exceeds a threshold and to control the light-steering system according to whether the apparatus motion exceeds the threshold.

According to some examples, the control system 106 may be configured to control the light-steering system 105 to compensate for the apparatus motion. For example, if the control system 106 determines that the apparatus 100 has moved, or is moving, relative to a target object in contact with the apparatus, the control system 106 may be configured to control the light-steering system 105 to compensate for the apparatus motion. In one such example, if the control system 106 determines that the apparatus 100 has moved by 3 spatial units in the x direction and 4 spatial units in the y direction relative to the target object, the control system 106 may be configured to control the light-steering system 105 to direct light emitted by at least a first light source of the light source system 104 to a new plurality of areas that are shifted 3 spatial units along the x axis and 4 spatial units along the y axis from a previous plurality of areas.

The apparatus 100 may be used in a variety of different contexts, many examples of which are disclosed herein. For example, in some implementations a mobile device may include the apparatus 100. In some such examples, the mobile device may be a smart phone. In some implementations, a wearable device may include the apparatus 100. The wearable device may, for example, be a bracelet, an armband, a wristband, a watch, a ring, a headband or a patch. Accordingly, in some examples the apparatus 100 may be configured to be worn by, or attached to, a person.

Figure 2:
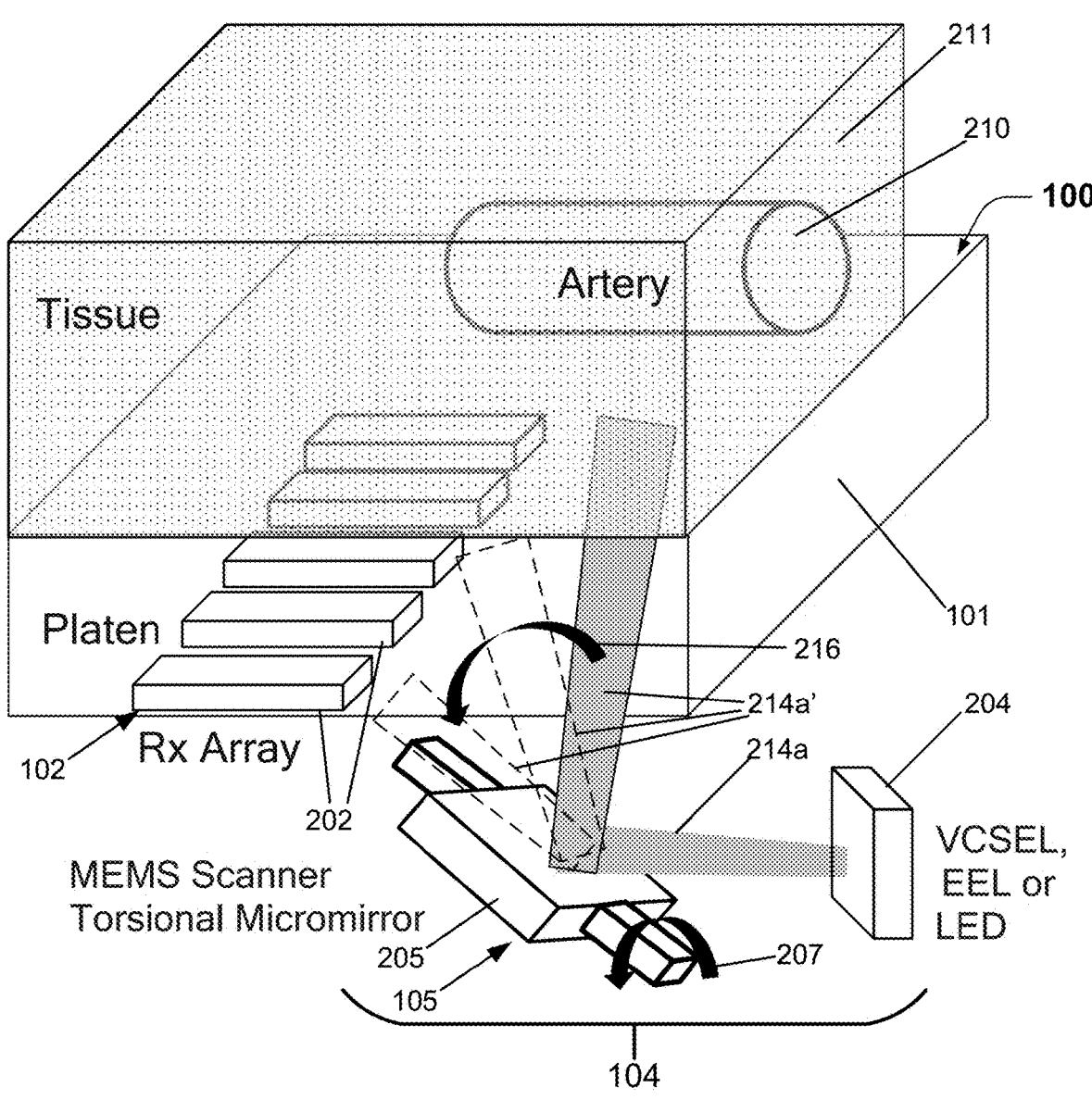
FIG. 2 shows an example of an apparatus that includes a light source system having a light-steering system.

FIG. 2 shows an example of an apparatus that includes a light source system having a light-steering system. As with other disclosed examples, the types, numbers, sizes and arrangements of elements shown in FIG. 2 and described herein are merely examples. According to this example, the apparatus 100 includes a platen 101, an ultrasonic receiver system 102, a light source system 104 and a control system 106 (not shown). In the example shown in FIG. 2, the light source system 104 includes at least the light source 204, which is a laser light source in this instance, and at least one light-steering device 205, which is a movable MEMS micromirror in this instance. The light source 204 may be, or may include, a VSCEL, an EEL or a laser diode (LD). According to this example, the ultrasonic receiver system 102 includes an array of receiver elements 202. In this example, the array includes five receiver elements 202. Other examples may include more or fewer than five receiver elements 202.

In this example, human tissue 211 is on an outer surface of the apparatus 100, touching the platen 101. Here, an artery 210 resides within the human tissue 211. The human tissue 211 is one example of what may be referred to herein as a "target object."

According to this example, the light-steering system 105 is configured to direct light emitted by at least the light source 204 to a plurality of areas of the target object. Here, the light-steering system 105 is configured to direct the light 214a emitted by the light source 204 as reflected light 214a' towards multiple areas of the target object. The arrow 216 indicates a range over which the light-steering system 105 is configured to provide the reflected light 214a' to the target object and the arrow 207 indicates a range of positions in which the light-steering system 105 may be positioned. In FIG. 2, the reflected light 214a' that the light-steering system 105 is currently directing towards the tissue 211 is shown with a solid outline and with gray fill, whereas other instances of the reflected light 214a', which the light-steering system 105 can direct towards other areas of the tissue 211 when the light-steering system 105 is positioned differently, is shown with a dashed outline and without fill. In some such examples, the control system 106 may be configured to control the light-steering system 105 to direct light from the light source 204 to the plurality of areas of the target object. For example, the control system 106 may be configured to control the light-steering system 105 to direct the reflected light 214a' light to 2, 3, 4, 5, 6, 7, 8, 9, 10, 11, 12, 13, 14, 15, 16, 17, 18, 19, 20 or more areas of the tissue 211.

According to some such examples, the control system 106 may be configured to receive signals from the ultrasonic receiver system 102 corresponding to each area of the target object that has been illuminated by the reflected light 214a'. The signals may correspond to ultrasonic waves caused by photoacoustic responses of each area of the target object that has been illuminated by the reflected light 214a'. In this example, the control system 106 is configured to receive signals from each of the receiver elements 202 in the array of ultrasonic receiver elements shown in FIG. 2.

According to some examples, the control system 106 may be configured to determine a selected area of the target object from which additional ultrasonic receiver signals will be obtained. In some such examples, the determining the selected area may involve detecting the artery 210, another blood vessel or another target of interest within the tissue 211. In some examples, determining the selected area may involve estimating a signal-to-noise ratio (SNR) of ultrasonic receiver signals corresponding to at least a portion of the artery 210. In some such examples, the control system 106 may be configured to determine the selected area by selecting an area corresponding to the highest SNR. According to some examples, the control system 106 may be configured to control the light source system 104 to obtain additional ultrasonic receiver signals from the selected area.

Figure 3:
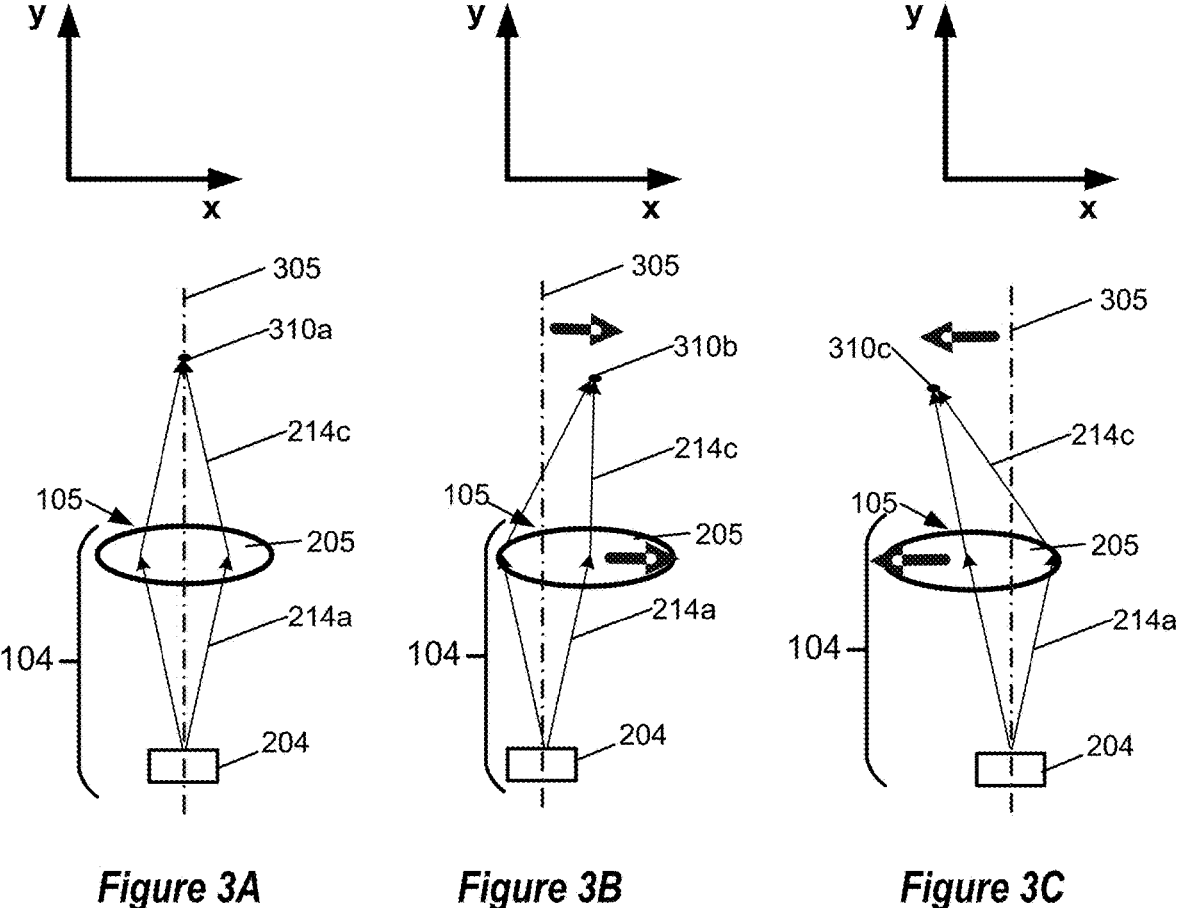
FIGS. 3A, 3B and 3C shows examples of a light source system that includes another type of light-steering system.

FIGS. 3A, 3B and 3C shows examples of a light source system that includes another type of light-steering system. As with other disclosed examples, the types, numbers, sizes and arrangements of elements shown in FIGS. 3A-3C and described herein are merely examples. According to these examples, light source system 104 includes a light-steering system 105 having at least one light-steering device 205, which is a movable lens in this instance. The light source 204 may be, or may include, a VSCEL, an EEL or a laser diode.

According to these examples, the light-steering system 105 is configured to direct light emitted by at least the light source 204 to a plurality of areas of a target object (not shown). In these examples, the light-steering system 105 is configured to direct the light 214a emitted by the light source 204 as refracted light 214c towards multiple areas of the target object.

In the example shown in FIG. 3A, the light-steering device 205 is shown directing the refracted light 214c towards an area 310a that coincides with the axis 305. In this example, the axis 305 is parallel with the y axis of the coordinate system shown in FIGS. 3A-3C.

In the example shown in FIG. 3B, the light-steering device 205 is shown directing the refracted light 214c towards an area 310b that is offset in the positive x direction relative to the axis 305 and relative to the coordinate system shown in FIGS. 3A-3C. Here, the light-steering device 205 is also offset in the positive x direction relative to the axis 305 and the coordinate system.

According to the example shown in FIG. 3C, the light-steering device 205 is shown directing the refracted light 214c towards an area 310c that is offset in the negative x direction relative to the axis 305 and the coordinate system. Here, the light-steering device 205 is also offset in the negative x direction relative to the axis 305.

Figure 4:
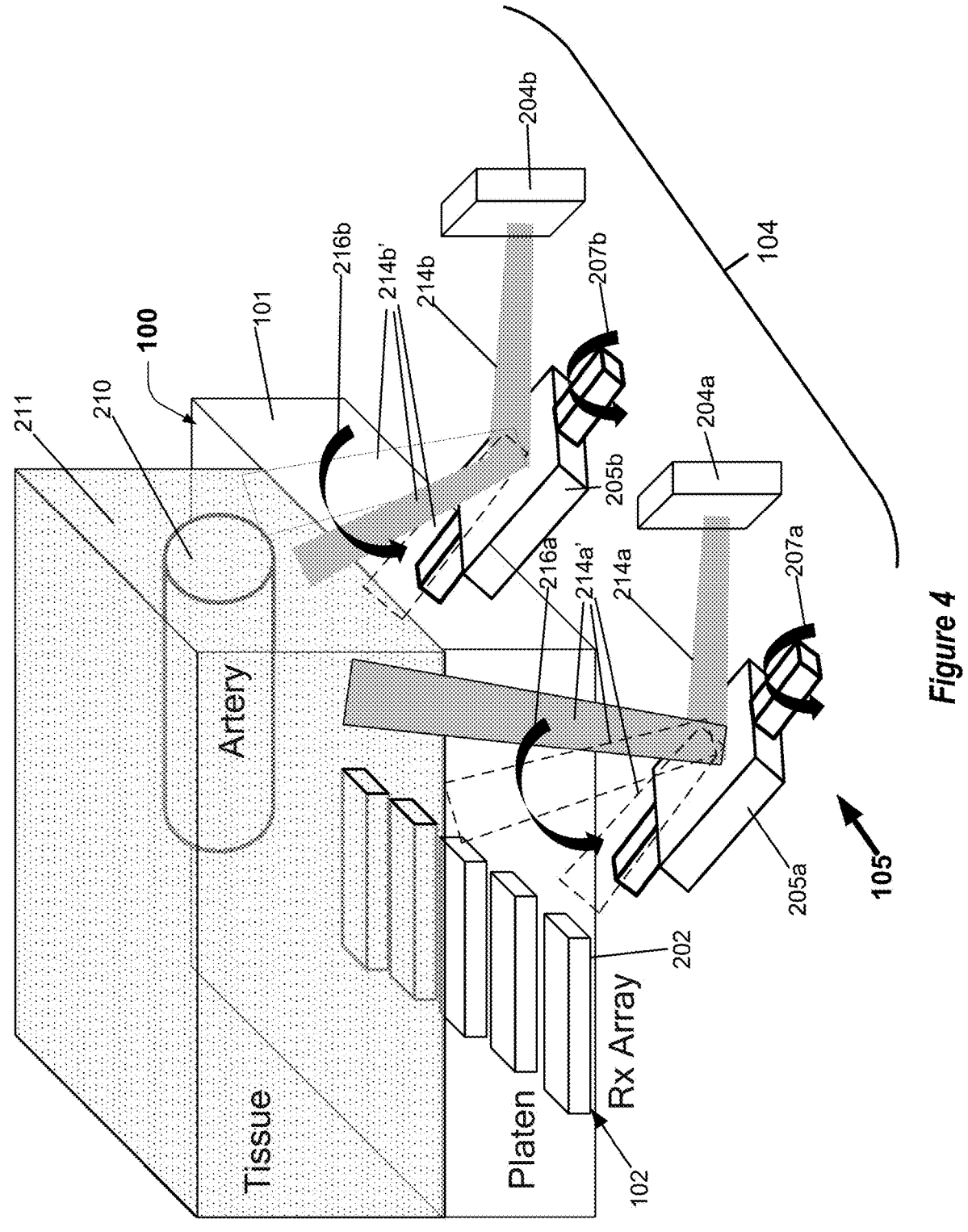
FIG. 4 shows another example of a light source system that includes a light-steering system.

FIG. 4 shows another example of a light source system that includes a light-steering system. As with other disclosed examples, the types, numbers, sizes and arrangements of elements shown in FIG. 4 and described herein are merely examples. According to this example, the apparatus 100 includes a platen 101, an ultrasonic receiver system 102, a light source system 104 and a control system 106 (not shown). In the example shown in FIG. 4, the light source system 104 includes at least the light sources 204a and 204b, which are laser light sources in this instance, and at least the light-steering devices 205a and 205b, which are movable MEMS micromirrors in this instance. According to this example, the ultrasonic receiver system 102 includes an array of receiver elements 202.

In this example, human tissue 211 is on an outer surface of the apparatus 100, touching the platen 101. According to this example, an artery 210 resides within the human tissue 211. In this example, the light-steering system 105 is configured to direct light emitted by the light sources 204a and 204b to a plurality of areas of the target object. Here, the light-steering device 205a is configured to reflect the light 214a emitted by the light source 204a as reflected light 214a' towards a first plurality of areas of the target object. Similarly, the light-steering device 205b is configured to reflect the light 214b emitted by the light source 204b as reflected light 214b' towards a second plurality of areas of the target object. In some examples, the first plurality of areas may be the same as the second plurality of areas, whereas in other examples the first plurality of areas may be different from the second plurality of areas. According to some such examples, the light-steering system 105 may be configured to direct the first light to the first plurality of areas at a first time and configured to direct the second light to the second plurality of areas at a second time that is different from the first time. In some such examples, the first light may have a peak amplitude at a first wavelength and the second light may have a peak amplitude at a second wavelength. The arrows 216a and 216b indicate ranges over which the light-steering devices 205a and 205b are configured to provide the reflected light 214a' and 214b'. Here, the arrows 207a and 207b indicate ranges over which the light-steering devices 205a and 205b are configured to be positioned, in this example by rotating the light-steering devices 205a and 205b. In some examples, the light-steering system 105 may include the light-steering devices that can be both rotated and translated, or moved, relative to the platen 101 and relative to a target object on the platen 101.

According to some examples, the control system 106 may be configured to receive signals from the ultrasonic receiver system 102 corresponding to each area of the target object that is illuminated by the reflected light 214a' and 214b'. The signals may correspond to ultrasonic waves caused by photoacoustic responses of each area of the target object illuminated by the reflected light 214a' and 214b'. In this example, the control system 106 is configured to receive signals from each of the receiver elements 202 in the array of ultrasonic receiver elements shown in FIG. 4.

According to some examples, the control system 106 may be configured to determine a selected area of the target object from which additional ultrasonic receiver signals will be obtained. In some such examples, the determining the selected area may involve detecting the artery 210 within the tissue 211. In some examples, determining the selected area may involve estimating a signal-to-noise ratio (SNR) of ultrasonic receiver signals corresponding to at least a portion of the artery 210. In some such examples, the control system 106 may be configured to determine the selected area by selecting an area corresponding to the highest SNR. According to some examples, the control system 106 may be configured to control the light source system 104 to obtain additional ultrasonic receiver signals from the selected area.

Figure 5:
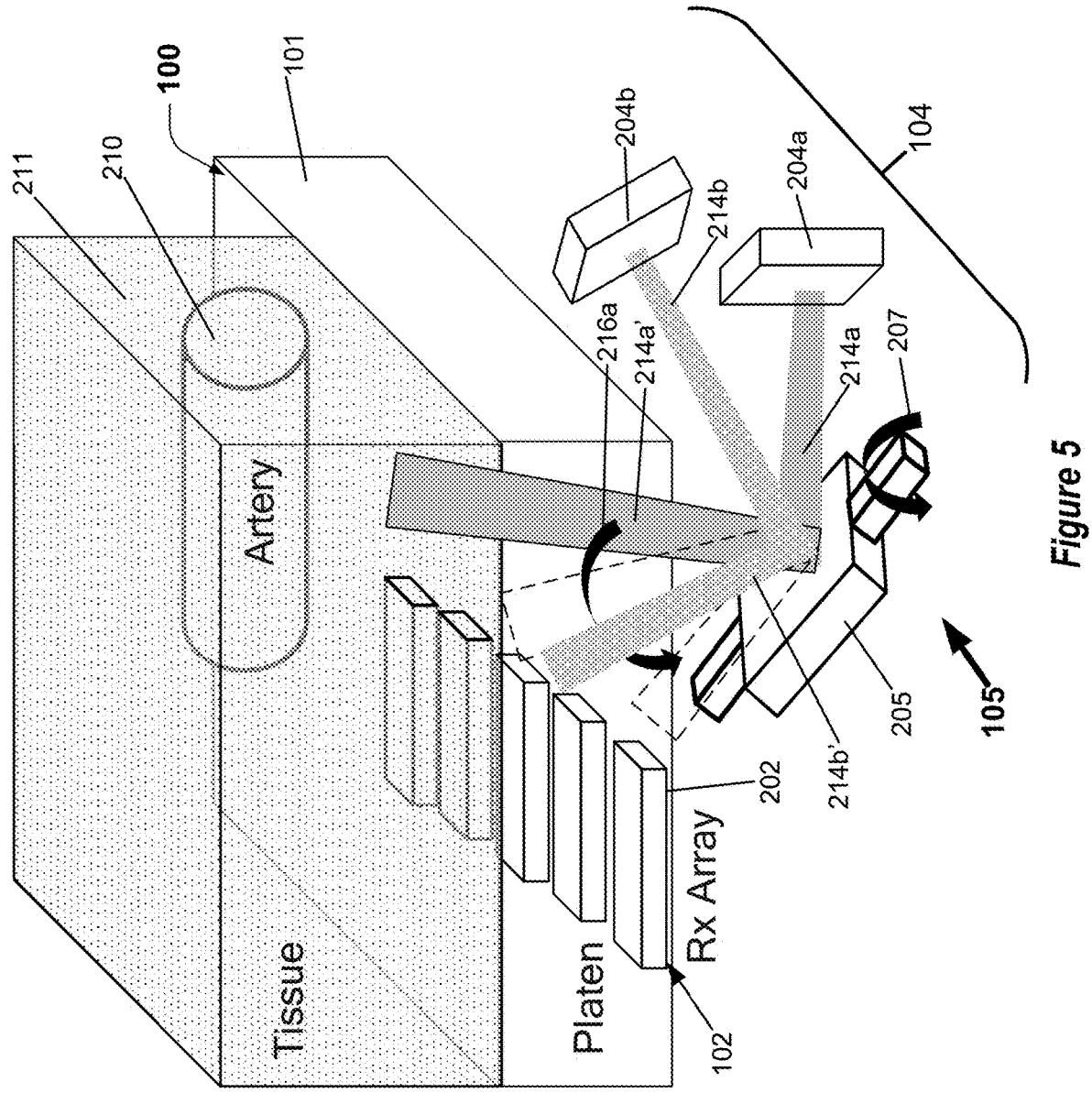
FIG. 5 shows another example of a light source system that includes a light-steering system.

FIG. 5 shows another example of a light source system that includes a light-steering system. As with other disclosed examples, the types, numbers, sizes and arrangements of elements shown in FIG. 5 and described herein are merely examples. According to this example, the apparatus 100 includes a platen 101, an ultrasonic receiver system 102, a light source system 104 and a control system 106 (not shown). In the example shown in FIG. 5, the light source system 104 includes at least the light sources 204a and 204b, which are a laser light sources in this instance, and at least the light-steering device 205, which is a movable MEMS micromirror in this instance. According to this example, the ultrasonic receiver system 102 includes an array of receiver elements 202.

In this example, the light-steering device 205 is configured to direct light emitted by the light sources 204*a* and 204*b* to a plurality of areas of the target object. Here, the light-steering device 205 is configured to reflect the light 214*a* emitted by the light source 204*a* as reflected light 214*a*' towards a first plurality of areas of the target object. Similarly, the light-steering device 205 is configured to reflect the light 214*b* emitted by the light source 204*b* as reflected light 214*b*' towards a second plurality of areas of the target object. In some examples, the first plurality of areas may be the same as the second plurality of areas, whereas in other examples the first plurality of areas may be different from the second plurality of areas. According to some such examples, the light-steering device 205 may be configured to direct the first light to the first plurality of areas at a first time and configured to direct the second light to the second plurality of areas at a second time that is different from the first time. In some such examples, the first light may have a peak amplitude at a first wavelength and the second light may have a peak amplitude at a second wavelength. The arrow 216*a* indicates a range over which the light-steering device 205 is configured to provide the reflected light 214*a*' and 214*b*'. In this example, the arrow 207 indicates a range of motion of the light-steering device 205.

According to some such examples, the control system 106 may be configured to receive signals from the ultrasonic receiver system 102 corresponding to each area of the target object that is illuminated by the reflected light 214*a*' and 214*b*'. The signals may correspond to ultrasonic waves caused by photoacoustic responses of each area of the target object illuminated by the reflected light 214*a*' and 214*b*'. In this example, the control system 106 is configured to receive signals from each of the receiver elements 202 in the array of ultrasonic receiver elements shown in FIG. 5.

According to some examples, the control system 106 may be configured to determine a selected area of the target object from which additional ultrasonic receiver signals will be obtained. In some such examples, the determining the selected area may involve detecting the artery 210 within the tissue 211. In some examples, determining the selected area may involve estimating a signal-to-noise ratio (SNR) of ultrasonic receiver signals corresponding to at least a portion of the artery 210. In some such examples, the control system 106 may be configured to determine the selected area by selecting an area corresponding to the highest SNR. According to some examples, the control system 106 may be configured to control the light source system 104 to obtain additional ultrasonic receiver signals from the selected area.

Figure 6:
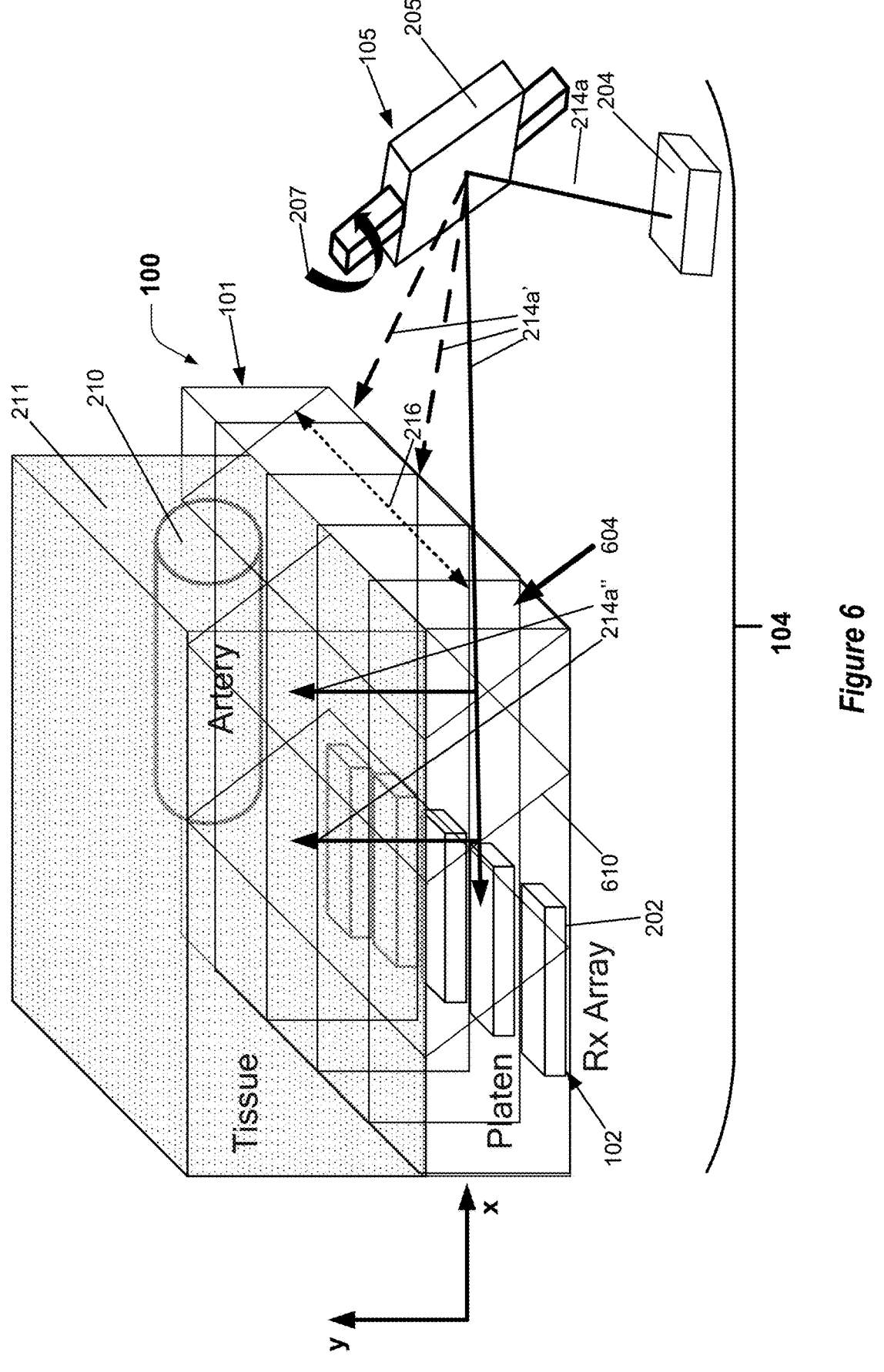
FIG. 6 shows another example of a light source system that includes a light-steering system.

FIG. 6 shows another example of a light source system that includes a light-steering system. As with other disclosed examples, the types, numbers, sizes and arrangements of elements shown in FIG. 6 and described herein are merely examples. According to this example, the apparatus 100 includes a platen 101, an ultrasonic receiver system 102, a light source system 104 and a control system 106 (not shown). In the example shown in FIG. 6, the light source system 104 includes at least the light source 204, which is a laser light source in this instance, and at least one light-steering device 205, which is a movable MEMS micromirror in this instance.

In this example, the light source system 104 includes a plurality of light guides 604. According to this example, the light-steering system 105 is configured to direct light 214*a* emitted by the light source 204 as reflected light 214*a*' to each of the plurality of light guides 604. In this example, the arrow 207 indicates a range of motion of the light-steering device 205 and the arrow 216 indicates a range over which the light-steering device 205 is configured to provide the reflected light 214' to the plurality of light guides 604. According to this example, the platen 101 includes the light guides 604. Therefore, the light guides 604 may be considered to be part of the platen 101, to be part of the light source system 104, or both.

According to this example, the ultrasonic receiver system 102 includes an array of receiver elements 202. In this example, the array includes five receiver elements 202. In this example, one receiver element 202 corresponds to one light guide 604 of the plurality of light guides. For example, one receiver element 202 may be positioned proximate one light guide 604, another receiver element 202 may be positioned proximate another light guide 604, and so on. Other examples may include more or fewer than five receiver elements 202, different arrangements of receiver elements 202 relative to light guides 604, or combinations thereof.

In this example, each light guide 604 is configured to direct a first portion of received light—here, the reflected light 214*a*'—along an axis of the light guide 604, which corresponds with the x axis in this example. According to this example, each light guide 604 is configured to direct a second portion of the received light—here, the extracted light 214*a*"—towards a target object, which is the tissue 211 in this example. In this example, each light guide 604 includes a plurality of light-extracting elements 610, which are configured to extract at least some of the reflected light 214*a*' and to direct the extracted light 214*a*" towards the tissue 211.

According to some such examples, the control system 106 may be configured to receive signals from the ultrasonic receiver system 102 corresponding to each area of the target object that is illuminated by the reflected light 214*a*". The signals may correspond to ultrasonic waves caused by photoacoustic responses of each area of the target object illuminated by the reflected light 214*a*". In this example, the control system 106 is configured to receive signals from each of the receiver elements 202 in the array of ultrasonic receiver elements shown in FIG. 6.

Figure 7:
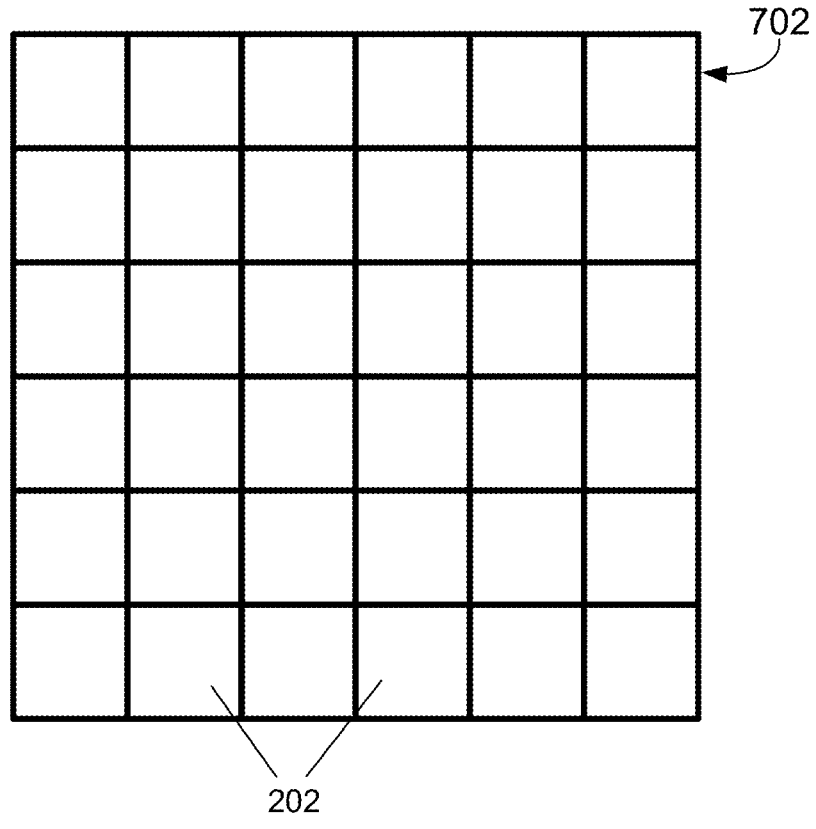
FIG. 7 shows an example of an ultrasonic receiver element array.

FIG. 7 shows an example of an ultrasonic receiver element array. In this example, the array of ultrasonic receiver elements 702 is a two-dimensional array of ultrasonic receiver elements. According to this example, the array of ultrasonic receiver elements 702 is arranged in a square having 6 active ultrasonic receiver elements 202 on each side and a total of 36 active ultrasonic receiver elements 202. As with other disclosed examples, the type, number, size and arrangement of elements shown in FIG. 7 and described herein are merely examples. For example, alternative examples of two-dimensional arrays of ultrasonic receiver elements may be arranged in a different shape, such as a non-square rectangular shape, a hexagonal shape, etc. Some alternative examples of two-dimensional arrays of ultrasonic receiver elements may include a different number of active ultrasonic receiver elements 202, such as 16, 20, 25, 30, 32, 36, 40, 48, etc.

Figure 8:
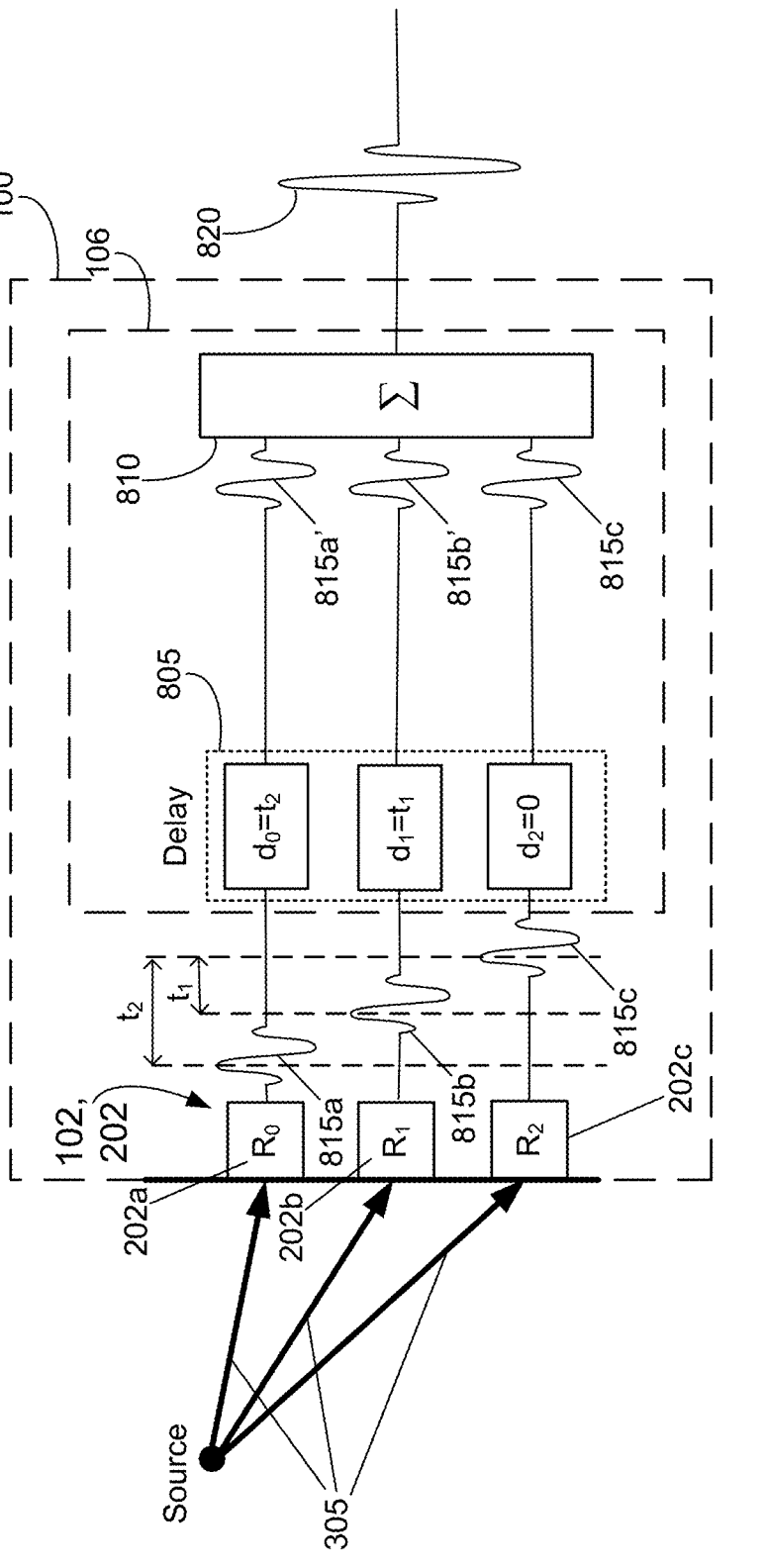
FIG. 8 shows an example of an apparatus that is configured to perform a receiver-side beamforming process.

FIG. 8 shows an example of an apparatus that is configured to perform a receiver-side beamforming process. In this example, the receiver-side beamforming process is a delay-and-sum beamforming process. As with other disclosed examples, the types, numbers, sizes and arrangements of elements shown in FIG. 8 and described herein, as well as the associated described methods, are merely examples.

In this example, a source is shown emitting ultrasonic waves 305, which are detected by active ultrasonic receiver elements 202a, 202b and 202c of an array of ultrasonic receiver elements 202. The array of ultrasonic receiver elements 202 is part of an ultrasonic receiver system 102. The ultrasonic waves 305 may, in some examples, correspond to the photoacoustic response of a target object to light emitted by a light source system 104 of the apparatus 101. In this example, the active ultrasonic receiver elements 202a, 202b and 202c provide ultrasonic receiver signals 815a, 815b and 815c, respectively, to the control system 106.

According to this example, the control system 106 includes a delay module 805 and a summation module 810. In this example, the delay module 805 is configured to determine whether a delay should be applied to each of the ultrasonic receiver signals 815a, 815b and 815c, and if so, what delay will be applied. According to this example, the delay module 805 determines that a delay $d_0$ of $t_2$ should be applied to the ultrasonic receiver signal 815a, that a delay $d_1$ of $t_1$ should be applied to the ultrasonic receiver signal 815b and that no delay should be applied to the ultrasonic receiver signal 815c. Accordingly, the delay module 805 applies a delay of $t_2$ to the ultrasonic receiver signal 815a, producing the ultrasonic receiver signal 815a', and applies a delay of $t_1$ to the ultrasonic receiver signal 815b, producing the ultrasonic receiver signal 815b'.

In some examples, the delay module 805 may determine what delay, if any, to apply to an ultrasonic receiver signal by performing a correlation operation on input ultrasonic receiver signals. For example, the delay module 805 may perform a correlation operation on the ultrasonic receiver signals 815a and 815c, and may determine that by applying a time shift of $t_2$ to the ultrasonic receiver signal 815a, the ultrasonic receiver signal 815a would be strongly correlated with the ultrasonic receiver signal 815c. Similarly, the delay module 805 may perform a correlation operation on the ultrasonic receiver signals 815b and 815c, and may determine that by applying a time shift of $t_1$ to the ultrasonic receiver signal 815b, the ultrasonic receiver signal 815b would be strongly correlated with the ultrasonic receiver signal 815c.

According to this example, the summation module 810 is configured to sum the ultrasonic receiver signals 815a', 815b' and 815c, producing the summed signal 820. One may observe that the amplitude of the summed signal 820 is greater than the amplitude of any one of the ultrasonic receiver signals 815a. 815b or 815c. In some instances, the signal-to-noise ratio (SNR) of the summed signal 820 may be greater than the SNR of any of the ultrasonic receiver signals 815a, 815b or 815c.

FIG. 9 is a flow diagram that shows examples of some disclosed operations. The blocks of FIG. 9 may, for example, be performed by the apparatus 100 of FIG. 1 or by a similar apparatus. In some examples, some or all blocks of FIG. 9 may be performed by the control system 106. As with other methods disclosed herein, the method outlined in FIG. 9 may include more or fewer blocks than indicated. Moreover, the blocks of methods disclosed herein are not necessarily performed in the order indicated. In some instances, one or more of the blocks shown in FIG. 9 may be performed concurrently.

In this example, block 905 involves controlling a light-steering system to direct light emitted by at least a first light source of a light source system to a first plurality of areas of a target object. According to this example, controlling the light-steering system involves controlling one or more adjustable micromirrors, one or more adjustable lenses, one or more adjustable diffraction gratings, or combinations thereof. The target object may be a finger, a wrist, etc., depending on the particular example.

According to this example, block 910 involves receiving ultrasonic receiver signals from an ultrasonic receiver system corresponding to photoacoustic responses of the target object to light provided the light source system to each area of the first plurality of areas. In this example, the ultrasonic receiver signals correspond to ultrasonic waves generated by the target object responsive to the light from the light source system.

In this example, block 915 involves determining a selected area of the target object from which additional ultrasonic receiver signals will be obtained. According to this example, determining the selected area involves detecting a blood vessel within the target object. The blood vessel may, for example, be detected according to a time window that corresponds with the speed of sound traversing an expected range of depth to a blood vessel. Alternatively, or additionally, the blood vessel may be detected according to one or more characteristics of the photoacoustic responses of the blood vessel walls, of blood within the blood vessel, or a combination thereof. In some examples, determining the selected area may involve estimating a signal-to-noise ratio (SNR) of ultrasonic receiver signals corresponding to at least a portion of the blood vessel and selecting an area corresponding to a highest SNR.

According to this example, block 920 involves controlling the light source system to obtain additional ultrasonic receiver signals from the selected area.

In some examples, method 900 may involve controlling the light-steering system to direct light emitted by a second light source of the light source system to a second plurality of areas of the target object. The second plurality of areas may or may not correspond to, or be the same as, the first plurality of areas, depending on the particular implementation.

According to some examples, controlling the light-steering system may involve directing light emitted by at least the first light source to each light guide of a plurality of light guides. A platen, such as the platen 101 that is described with reference to FIG. 1 or FIG. 6 may, in some implementations, include the light guides.

In some examples, the ultrasonic receiver system 102 may include an array of ultrasonic receiver elements. In some such examples, method 900 may involve receiving ultrasonic receiver signals from each of a plurality of ultrasonic receiver elements in the array. According to some examples, the array of ultrasonic receiver elements may be, or may include, a linear array of ultrasonic receiver elements or a two-dimensional array of ultrasonic receiver elements. In some examples, the array of ultrasonic receiver elements may be, or may include, an array of electrodes arranged on a piezoelectric layer. In some instances, the piezoelectric layer may be, or may include, lead zirconate titanate (PZT) or a piezoelectric composite.

According to some examples, method 900 may involve applying, by the control system, a receiver-side beamforming process to the ultrasonic receiver signals, to produce a beamformed ultrasonic receiver image. In some examples, the receiver-side beamforming process may be, or may include, a delay-and-sum beamforming process. The receiver-side beamforming process may, for example, involve a process like that described with reference to FIG. 8.

According to some examples, method 900 may involve receive inertial sensor data from an inertial sensor system— such as the inertial sensor system 112 of FIG. 1—and control the light-steering system based, at least in part, on the inertial sensor data. For example, method 900 may involve determining whether the inertial sensor data indicates motion of the apparatus 100 that exceeds a threshold and controlling the light-steering system 105 according to whether the apparatus motion exceeds the threshold.

In some examples, method 900 may involve controlling the light-steering system 105 to compensate for the apparatus motion. For example, if the control system 106 determines that the apparatus 100 has moved, or is moving, relative to a target object in contact with the apparatus, method 900 may involve controlling the light-steering system 105 to compensate for the apparatus motion. In one such example, if the control system 106 determines that the apparatus 100 has moved by 5 spatial units in the x direction and 2 spatial units in the y direction relative to the target object, method 900 may involve controlling the light-steering system 105 to direct light emitted by at least a first light source of the light source system 104 to a new plurality of areas that are shifted 5 spatial units along the x axis and 2 spatial units along the y axis from a previous plurality of areas.

In some examples, method 900 may involve estimating one or more blood vessel features based, at least in part, on the additional ultrasonic receiver signals. The one or more blood vessel features may, for example, include blood vessel diameter, blood vessel distention, volumetric flow, pulse wave velocity, blood vessel wall thickness, or combinations thereof. The one or more blood vessel features may, in some examples, be arterial features. In some examples, method 900 may involve estimating one or more cardiac features based, at least in part, on the one or more blood vessel features. According to some such examples, method 900 may involve estimating blood pressure based, at least in part, on the one or more blood vessel features. According to some examples, method 900, may involve extracting and evaluating heart rate waveform (HRW) features.

Figure 11:
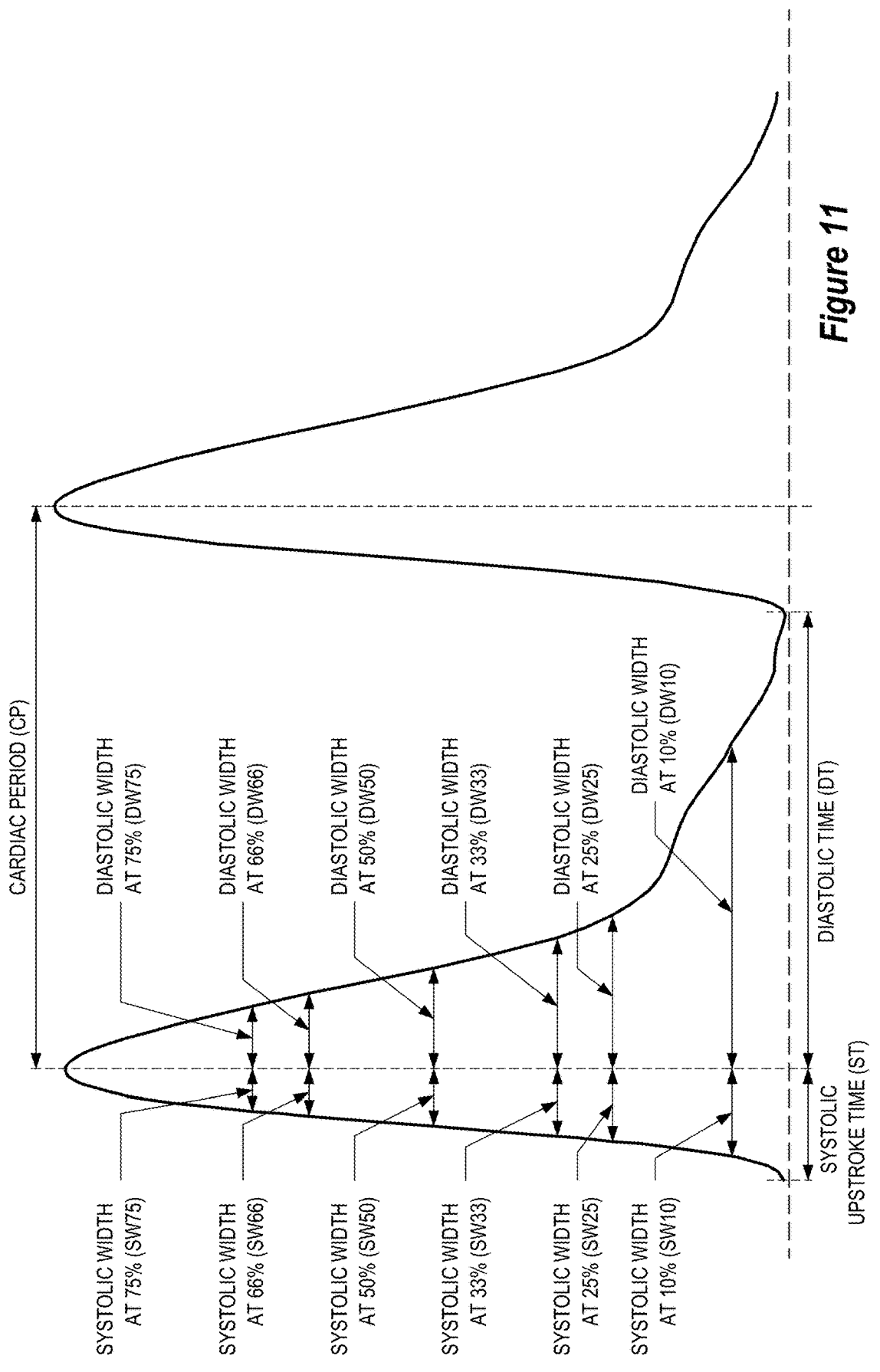
FIG. 11 shows examples of heart rate waveform (HRW) features that may be extracted according to some implementations of the method of FIG. 9.

FIG. 11 shows examples of heart rate waveform (HRW) features that may be extracted according to some implementations of the method of FIG. 9. The horizontal axis of FIG. 11 represents time and the vertical axis represents signal amplitude. The cardiac period is indicated by the time between adjacent peaks of the HRW. The systolic and diastolic time intervals are indicated below the horizontal axis. During the systolic phase of the cardiac cycle, as a pulse propagates through a particular location along an artery, the arterial walls expand according to the pulse waveform and the elastic properties of the arterial walls. Along with the expansion is a corresponding increase in the volume of blood at the particular location or region, and with the increase in volume of blood an associated change in one or more characteristics in the region. Conversely, during the diastolic phase of the cardiac cycle, the blood pressure in the arteries decreases and the arterial walls contract. Along with the contraction is a corresponding decrease in the volume of blood at the particular location, and with the decrease in volume of blood an associated change in the one or more characteristics in the region.

The HRW features that are illustrated in FIG. 11 pertain to the width of the systolic and/or diastolic portions of the HRW curve at various "heights," which are indicated by a percentage of the maximum amplitude. For example, the SW50 feature is the width of the systolic portion of the HRW curve at a "height" of 50% of the maximum amplitude. In some implementations, the HRW features used for blood pressure estimation may include some or all of the SW10, SW25, SW33, SW50, SW66, SW75, DW10, DW25, DW33, DW50, DW66 and DW75 HRW features. In other implementations, additional HRW features may be used for blood pressure estimation. Such additional HRW features may, in some instances, include the sum and ratio of the SW and DW at one or more "heights," e.g., (DW75+SW75), DW75/SW75, (DW66+SW66), DW66/SW66, (DW50+SW50), DW50/SW50, (DW33+SW33), DW33/SW33, (DW25+SW25), DW25/SW25 and/or (DW10+SW10), DW10/SW10. Other implementations may use yet other HRW features for blood pressure estimation. Such additional HRW features may, in some instances, include sums, differences, ratios and/or other operations based on more than one "height," such as (DW75+SW75)/(DW50+SW50), (DW50+SW50/(DW10+SW10), etc.

Figure 12:
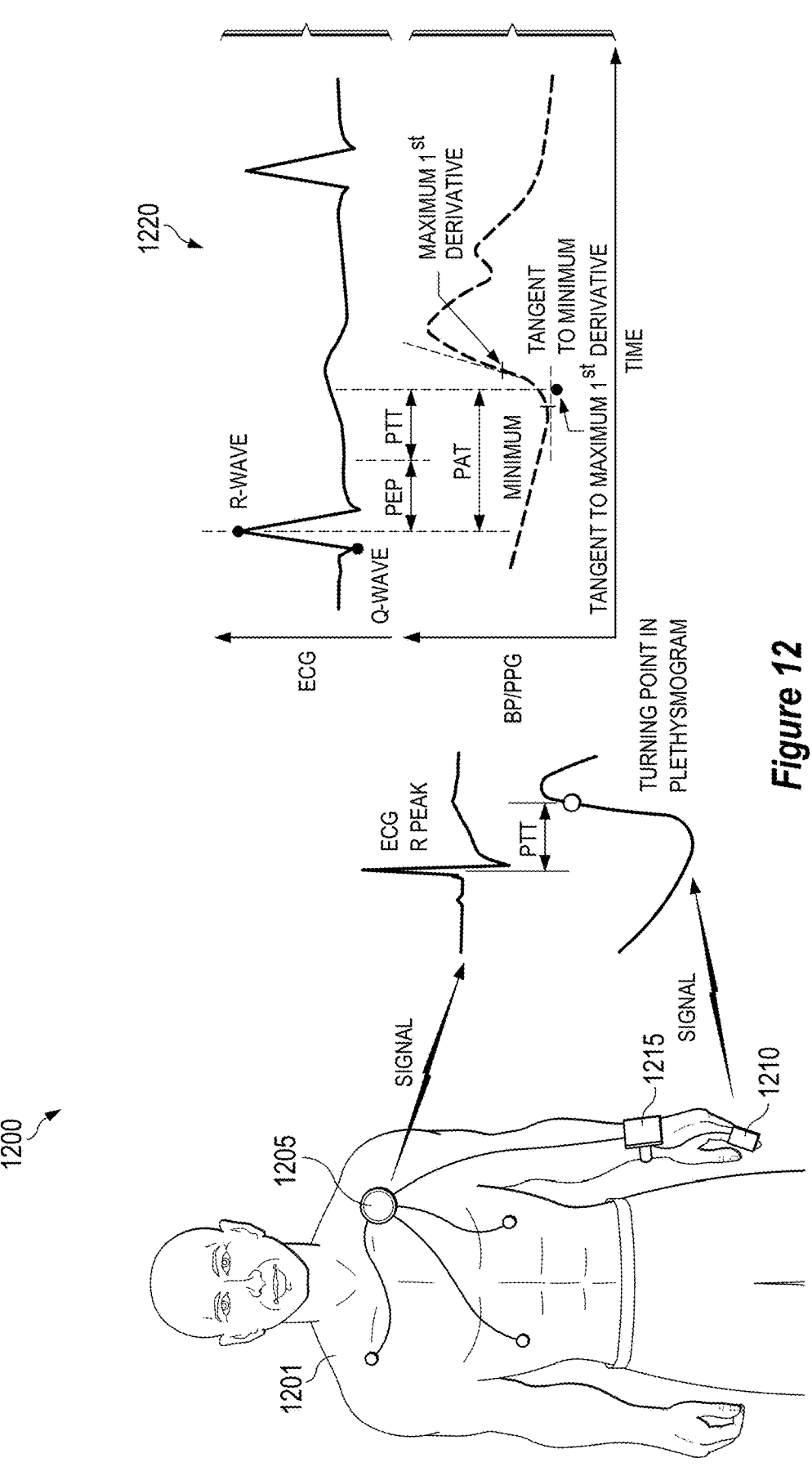
FIG. 12 shows examples of devices that may be used in a system for estimating blood pressure based, at least in part, on pulse transit time (PTT).

FIG. 12 shows examples of devices that may be used in a system for estimating blood pressure based, at least in part, on pulse transit time (PTT). As with other figures provided herein, the numbers, types and arrangements of elements are merely presented by way of example. According to this example, the system 1200 includes at least two sensors. In this example, the system 1200 includes at least an electrocardiogram sensor 1205 and a device 1210 that is configured to be mounted on a finger of the person 1201. In this example, the device 1210 is, or includes, an apparatus configured to perform at least some PAPG methods disclosed herein. For example, the device 1210 may be, or may include, the apparatus 300 of FIG. 3 or a similar apparatus.

As noted in the graph 1220, the PAT includes two components, the pre-ejection period (PEP, the time needed to convert the electrical signal into a mechanical pumping force and isovolumetric contraction to open the aortic valves) and the PTT. The starting time for the PAT can be estimated based on the QRS complex—an electrical signal characteristic of the electrical stimulation of the heart ventricles. As shown by the graph 1220, in this example the beginning of a pulse arrival time (PAT) may be calculated according to an R-Wave peak measured by the electrocardiogram sensor 1205 and the end of the PAT may be detected via analysis of signals provided by the device 1210. In this example, the end of the PAT is assumed to correspond with an intersection between a tangent to a local minimum value detected by the device 1210 and a tangent to a maximum slope/first derivative of the sensor signals after the time of the minimum value.

There are many known algorithms for blood pressure estimation based on the PTT and/or the PAT, some of which are summarized in Table 1 and described in the corresponding text on pages 5-10 of Sharma, M., et al., *Cuff-Less and Continuous Blood Pressure Monitoring: a Methodological Review* ("Sharma"), in Multidisciplinary Digital Publishing Institute (MDPI) Technologies 2017, 5, 21, both of which are hereby incorporated by reference.

Some previously-disclosed methods have involved calculating blood pressure according to one or more of the equations shown in Table 1 of Sharma, or other known equations, based on a PTT and/or PAT measured by a sensor system that includes a PPG sensor. As noted above, some disclosed PAPG-based implementations are configured to distinguish artery HRWs from other HRWs. Such implementations may provide more accurate measurements of the PTT and/or PAT, relative to those measured by a PPG sensor.

Therefore, disclosed PAPG-based implementations may provide more accurate blood pressure estimations, even when the blood pressure estimations are based on previously-known formulae.

Other implementations of the system 1200 may not include the electrocardiogram sensor 1205. In some such implementations, the device 1215, which is configured to be mounted on a wrist of the person 1201, may be, or may include, an apparatus configured to perform at least some PAPG methods disclosed herein. For example, the device 1215 may be, or may include, the apparatus 200 of FIG. 2 or a similar apparatus. According to some such examples, the device 1215 may include a light source system and two or more ultrasonic receivers. One example is described below with reference to FIG. 14A. In some examples, the device 1215 may include an array of ultrasonic receivers.

In some implementations of the system 1200 that $d_0$ not include the electrocardiogram sensor 1205, the device 1210 may include a light source system and two or more ultrasonic receivers. One example is described below with reference to FIG. 14B.

Figure 13:
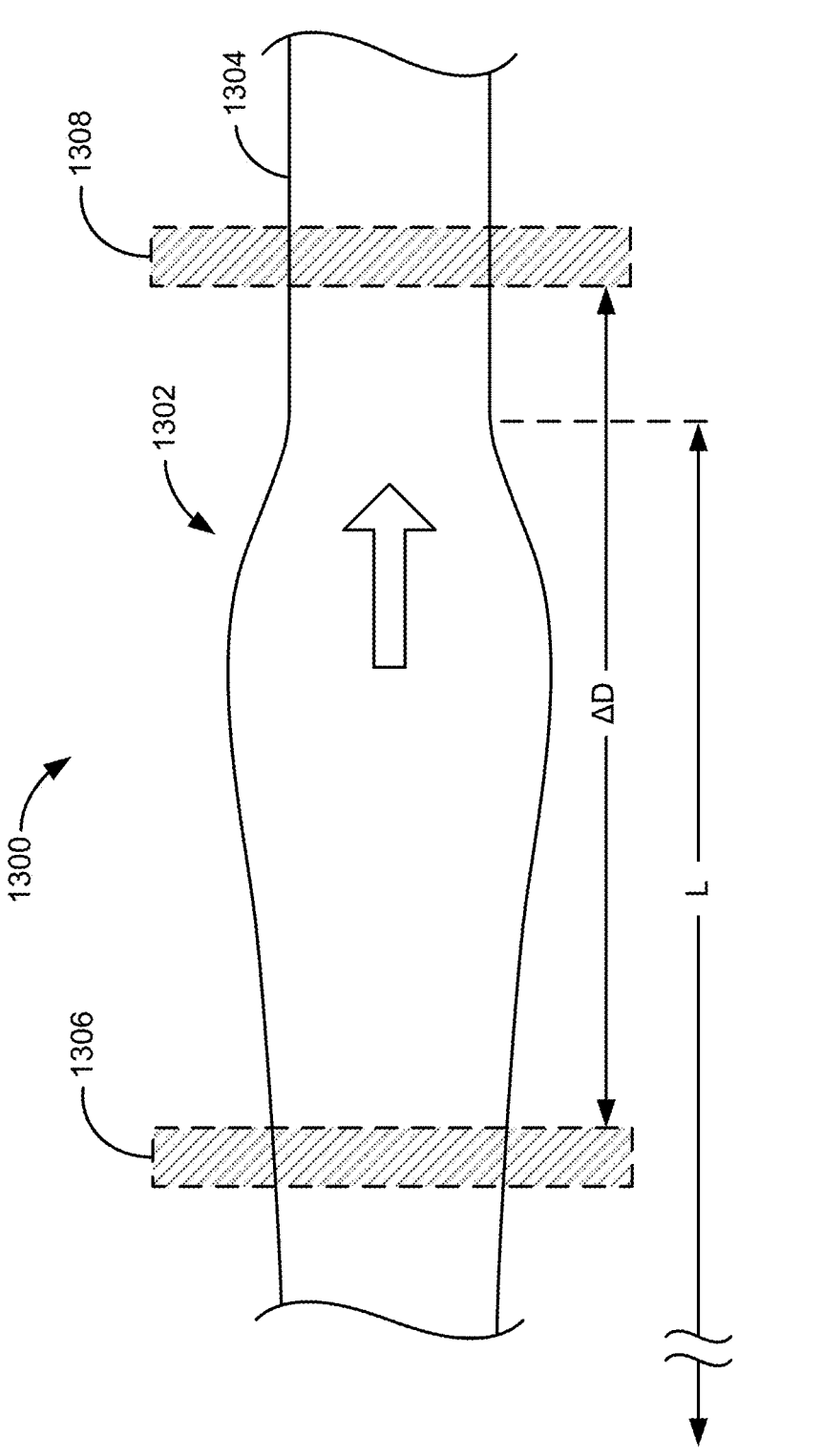
FIG. 13 shows a cross-sectional side view of a diagrammatic representation of a portion of an artery through which a pulse is propagating.

FIG. 13 shows a cross-sectional side view of a diagrammatic representation of a portion of an artery 1300 through which a pulse 1302 is propagating. The block arrow in FIG. 13 shows the direction of blood flow and pulse propagation. As diagrammatically shown, the propagating pulse 1302 causes strain in the arterial walls 1304, which is manifested in the form of an enlargement in the diameter (and consequently the cross-sectional area) of the arterial walls-referred to as "distension." The spatial length L of an actual propagating pulse along an artery (along the direction of blood flow) is typically comparable to the length of a limb, such as the distance from a subject's shoulder to the subject's wrist or finger, and is generally less than one meter (m). However, the length L of a propagating pulse can vary considerably from subject to subject, and for a given subject, can vary significantly over durations of time depending on various factors. The spatial length L of a pulse will generally decrease with increasing distance from the heart until the pulse reaches capillaries.

As described above, some particular implementations relate to devices, systems and methods for estimating blood pressure or other cardiovascular characteristics based on estimates of an arterial distension waveform. The terms "estimating," "measuring," "calculating," "inferring," "deducing," "evaluating," "determining" and "monitoring" may be used interchangeably herein where appropriate unless otherwise indicated. Similarly, derivations from the roots of these terms also are used interchangeably where appropriate; for example, the terms "estimate," "measurement," "calculation," "inference" and "determination" also are used interchangeably herein. In some implementations, the pulse, wave velocity (PWV) of a propagating pulse may be estimated by measuring the pulse transit time (PTT) of the pulse as it propagates from a first physical location along an artery to another more distal second physical location along the artery. It will be appreciated that this PTT is different from the PTT that is described above with reference to FIG. 15. However, either version of the PTT may be used for the purpose of blood pressure estimation. Assuming that the physical distance ΔD between the first and the second physical locations is ascertainable, the PWV can be estimated as the quotient of the physical spatial distance ΔD traveled by the pulse divided by the time (PTT) the pulse takes in traversing the physical spatial distance ΔD. Generally, a first sensor positioned at the first physical location is used to determine a starting time (also referred to herein as a "first temporal location") at which point the pulse arrives at or propagates through the first physical location. A second sensor at the second physical location is used to determine an ending time (also referred to herein as a "second temporal location") at which point the pulse arrives at or propagates through the second physical location and continues through the remainder of the arterial branch. In such examples, the PTT represents the temporal distance (or time difference) between the first and the second temporal locations (the starting and the ending times).

The fact that measurements of the arterial distension waveform are performed at two different physical locations implies that the estimated PWV inevitably represents an average over the entire path distance ΔD through which the pulse propagates between the first physical location and the second physical location. More specifically, the PWV generally depends on a number of factors including the density of the blood p, the stiffness E of the arterial wall (or inversely the elasticity), the arterial diameter, the thickness of the arterial wall, and the blood pressure. Because both the arterial wall elasticity and baseline resting diameter (for example, the diameter at the end of the ventricular diastole period) vary significantly throughout the arterial system, PWV estimates obtained from PTT measurements are inherently average values (averaged over the entire path length ΔD between the two locations where the measurements are performed).

In traditional methods for obtaining PWV, the starting time of the pulse has been obtained at the heart using an electrocardiogram (ECG) sensor, which detects electrical signals from the heart. For example, the starting time can be estimated based on the QRS complex—an electrical signal characteristic of the electrical stimulation of the heart ventricles. In such approaches, the ending time of the pulse is typically obtained using a different sensor positioned at a second location (for example, a finger). As a person having ordinary skill in the art will appreciate, there are numerous arterial discontinuities, branches, and variations along the entire path length from the heart to the finger. The PWV can change by as much as or more than an order of magnitude along various stretches of the entire path length from the heart to the finger. As such, PWV estimates based on such long path lengths are unreliable.

In various implementations described herein, PTT estimates are obtained based on measurements (also referred to as "arterial distension data" or more generally as "sensor data") associated with an arterial distension signal obtained by each of a first arterial distension sensor 1306 and a second arterial distension sensor 1308 proximate first and second physical locations, respectively, along an artery of interest. In some particular implementations, the first arterial distension sensor 1306 and the second arterial distension sensor 1308 are advantageously positioned proximate first and second physical locations between which arterial properties of the artery of interest, such as wall elasticity and diameter, can be considered or assumed to be relatively constant. In this way, the PWV calculated based on the PTT estimate is more representative of the actual PWV along the particular segment of the artery. In turn, the blood pressure P estimated based on the PWV is more representative of the true blood pressure. In some implementations, the magnitude of the distance ΔD of separation between the first arterial distension sensor 1306 and the second arterial distension sensor 1308 (and consequently the distance between the first and the second locations along the artery) can be in the range of about 1 centimeter (cm) to tens of centimeters-long enough to distinguish the arrival of the pulse at the first physical location from the arrival of the pulse at the second physical location, but close enough to provide sufficient assurance of arterial consistency. In some specific implementations, the distance ΔD between the first and the second arterial distension sensors 1306 and 1308 can be in the range of about 1 cm to about 30 cm, and in some implementations, less than or equal to about 20 cm, and in some implementations, less than or equal to about 10 cm, and in some specific implementations less than or equal to about 5 cm. In some other implementations, the distance ΔD between the first and the second arterial distension sensors 1306 and 1308 can be less than or equal to 1 cm, for example, about 0.1 cm, about 0.25 cm, about 0.5 cm or about 0.75 cm. By way of reference, a typical PWV can be about 15 meters per second (m/s). Using an ambulatory monitoring device in which the first and the second arterial distension sensors 1306 and 1308 are separated by a distance of about 5 cm, and assuming a PWV of about 15 m/s implies a PTT of approximately 3.3 milliseconds (ms).

The value of the magnitude of the distance ΔD between the first and the second arterial distension sensors 1306 and 1308, respectively, can be preprogrammed into a memory within a monitoring device that incorporates the sensors (for example, such as a memory of, or a memory configured for communication with, the control system 306 that is described above with reference to FIG. 3). As will be appreciated by a person of ordinary skill in the art, the spatial length L of a pulse can be greater than the distance ΔD from the first arterial distension sensor 1306 to the second arterial distension sensor 1308 in such implementations. As such, although the diagrammatic pulse 1302 shown in FIG. 13 is shown as having a spatial length L comparable to the distance between the first arterial distension sensor 1306 and the second arterial distension sensor 1308, in actuality each pulse can typically have a spatial length L that is greater and even much greater than (for example, about an order of magnitude or more than) the distance ΔD between the first and the second arterial distension sensors 1306 and 1308.

Sensing Architecture and Topology

In some implementations of the ambulatory monitoring devices disclosed herein, both the first arterial distension sensor 1306 and the second arterial distension sensor 1308 are sensors of the same sensor type. In some such implementations, the first arterial distension sensor 1306 and the second arterial distension sensor 1308 are identical sensors. In such implementations, each of the first arterial distension sensor 1306 and the second arterial distension sensor 1308 utilizes the same sensor technology with the same sensitivity to the arterial distension signal caused by the propagating pulses, and has the same time delays and sampling characteristics. In some implementations, each of the first arterial distension sensor 1306 and the second arterial distension sensor 1308 is configured for photoacoustic plethysmography (PAPG) sensing, e.g., as disclosed elsewhere herein. Some such implementations include a light source system and two or more ultrasonic receivers, which may be instances of the light source system 104 and the receiver system 102 of FIG. 1. In some implementations, each of the first arterial distension sensor 1306 and the second arterial distension sensor 1308 is configured for ultrasound sensing via the transmission of ultrasonic signals and the receipt of corresponding reflections. In some alternative implementations, each of the first arterial distension sensor 1306 and the second arterial distension sensor 1308 may be configured for impedance plethysmography (IPG) sensing, also referred to in biomedical contexts as bioimpedance sensing. In various implementations, whatever types of sensors are utilized, each of the first and the second arterial distension sensors 1306 and 1308 broadly functions to capture and provide arterial distension data indicative of an arterial distension signal resulting from the propagation of pulses through a portion of the artery proximate to which the respective sensor is positioned. For example, the arterial distension data can be provided from the sensor to a processor in the form of voltage signal generated or received by the sensor based on an ultrasonic signal or an impedance signal sensed by the respective sensor.

As described above, during the systolic phase of the cardiac cycle, as a pulse propagates through a particular location along an artery, the arterial walls expand according to the pulse waveform and the elastic properties of the arterial walls. Along with the expansion is a corresponding increase in the volume of blood at the particular location or region, and with the increase in volume of blood an associated change in one or more characteristics in the region. Conversely, during the diastolic phase of the cardiac cycle, the blood pressure in the arteries decreases and the arterial walls contract. Along with the contraction is a corresponding decrease in the volume of blood at the particular location, and with the decrease in volume of blood an associated change in the one or more characteristics in the region.

In the context of bioimpedance sensing (or impedance plethysmography), the blood in the arteries has a greater electrical conductivity than that of the surrounding or adjacent skin, muscle, fat, tendons, ligaments, bone, lymph or other tissues. The susceptance (and thus the permittivity) of blood also is different from the susceptances (and permittivities) of the other types of surrounding or nearby tissues. As a pulse propagates through a particular location, the corresponding increase in the volume of blood results in an increase in the electrical conductivity at the particular location (and more generally an increase in the admittance, or equivalently a decrease in the impedance). Conversely, during the diastolic phase of the cardiac cycle, the corresponding decrease in the volume of blood results in an increase in the electrical resistivity at the particular location (and more generally an increase in the impedance, or equivalently a decrease in the admittance).

A bioimpedance sensor generally functions by applying an electrical excitation signal at an excitation carrier frequency to a region of interest via two or more input electrodes, and detecting an output signal (or output signals) via two or more output electrodes. In some more specific implementations, the electrical excitation signal is an electrical current signal injected into the region of interest via the input electrodes. In some such implementations, the output signal is a voltage signal representative of an electrical voltage response of the tissues in the region of interest to the applied excitation signal. The detected voltage response signal is influenced by the different, and in some instances time-varying, electrical properties of the various tissues through which the injected excitation current signal is passed. In some implementations in which the bioimpedance sensor is operable to monitor blood pressure, heartrate or other cardiovascular characteristics, the detected voltage response signal is amplitude- and phase-modulated by the time-varying impedance (or inversely the admittance) of the underlying arteries, which fluctuates synchronously with the user's heartbeat as described above. To determine various biological characteristics, information in the detected voltage response signal is generally demodulated from the excitation carrier frequency component using various analog or digital signal processing circuits, which can include both passive and active components.

In some examples incorporating ultrasound sensors, measurements of arterial distension may involve directing ultrasonic waves into a limb towards an artery, for example, via one or more ultrasound transducers. Such ultrasound sensors also are configured to receive reflected waves that are based, at least in part, on the directed waves. The reflected waves may include scattered waves, specularly reflected waves, or both scattered waves and specularly reflected waves. The reflected waves provide information about the arterial walls, and thus the arterial distension.

In some implementations, regardless of the type of sensors utilized for the first arterial distension sensor 1306 and the second arterial distension sensor 1308, both the first arterial distension sensor 1306 and the second arterial distension sensor 1308 can be arranged, assembled or otherwise included within a single housing of a single ambulatory monitoring device. As described above, the housing and other components of the monitoring device can be configured such that when the monitoring device is affixed or otherwise physically coupled to a subject, both the first arterial distension sensor 1306 and the second arterial distension sensor 1308 are in contact with or in close proximity to the skin of the user at first and second locations, respectively, separated by a distance ΔD, and in some implementations, along a stretch of the artery between which various arterial properties can be assumed to be relatively constant. In various implementations, the housing of the ambulatory monitoring device is a wearable housing or is incorporated into or integrated with a wearable housing. In some specific implementations, the wearable housing includes (or is connected with) a physical coupling mechanism for removable non-invasive attachment to the user. The housing can be formed using any of a variety of suitable manufacturing processes, including injection molding and vacuum forming, among others. In addition, the housing can be made from any of a variety of suitable materials, including, but not limited to, plastic, metal, glass, rubber and ceramic, or combinations of these or other materials. In particular implementations, the housing and coupling mechanism enable full ambulatory use. In other words, some implementations of the wearable monitoring devices described herein are non-invasive, not physically-inhibiting and generally do not restrict the free uninhibited motion of a subject's arms or legs, enabling continuous or periodic monitoring of cardiovascular characteristics such as blood pressure even as the subject is mobile or otherwise engaged in a physical activity. As such, the ambulatory monitoring device facilitates and enables long-term wearing and monitoring (for example, over days, weeks or a month or more without interruption) of one or more biological characteristics of interest to obtain a better picture of such characteristics over extended durations of time, and generally, a better picture of the user's health.

Figure 14A:
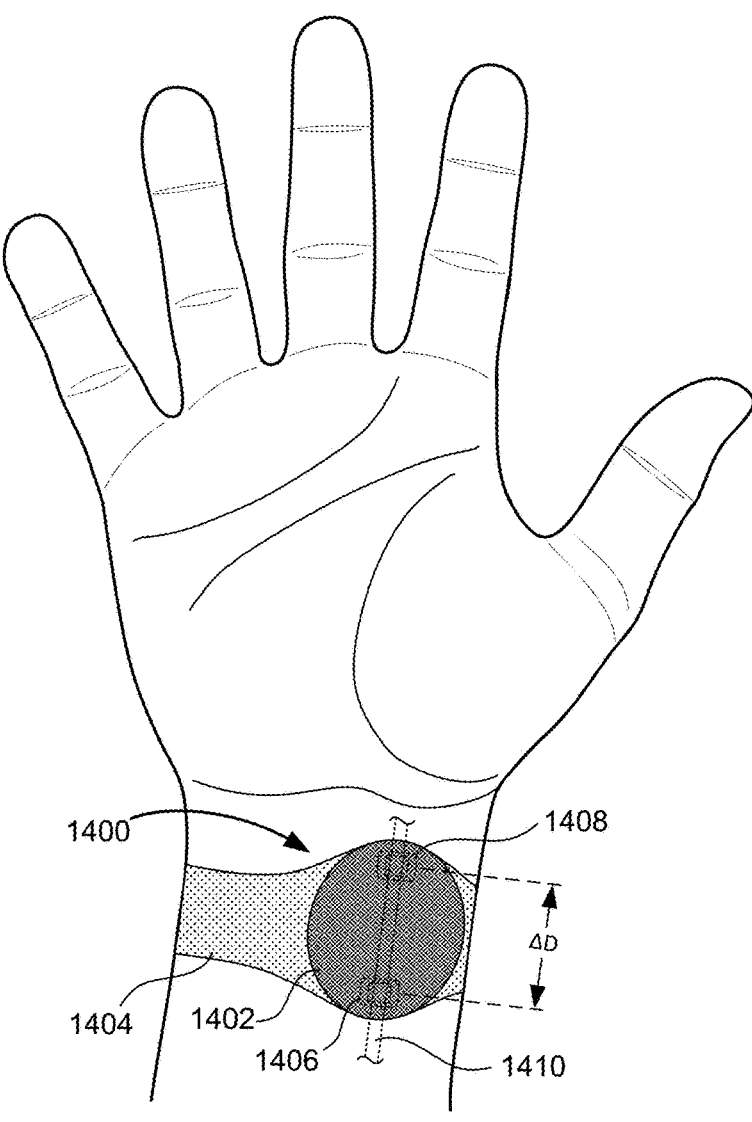
FIG. 14A shows an example ambulatory monitoring device designed to be worn around a wrist according to some implementations.

In some implementations, the ambulatory monitoring device can be positioned around a wrist of a user with a strap or band, similar to a watch or fitness/activity tracker. FIG. 14A shows an example ambulatory monitoring device 1400 designed to be worn around a wrist according to some implementations. In the illustrated example, the monitoring device 1400 includes a housing 1402 integrally formed with, coupled with or otherwise integrated with a wristband 1404. The first and the second arterial distension sensors 1406 and 1408 may, in some instances, each include an instance of the ultrasonic receiver system 302 and a portion of the light source system 304 that are described above with reference to FIG. 3. In this example, the ambulatory monitoring device 1400 is coupled around the wrist such that the first and the second arterial distension sensors 1406 and 1408 within the housing 1402 are each positioned along a segment of the radial artery 1410 (note that the sensors are generally hidden from view from the external or outer surface of the housing facing the subject while the monitoring device is coupled with the subject, but exposed on an inner surface of the housing to enable the sensors to obtain measurements through the subject's skin from the underlying artery). Also as shown, the first and the second arterial distension sensors 1406 and 1408 are separated by a fixed distance ΔD. In some other implementations, the ambulatory monitoring device 1400 can similarly be designed or adapted for positioning around a forearm, an upper arm, an ankle, a lower leg, an upper leg, or a finger (all of which are hereinafter referred to as "limbs") using a strap or band.

Figure 14B:
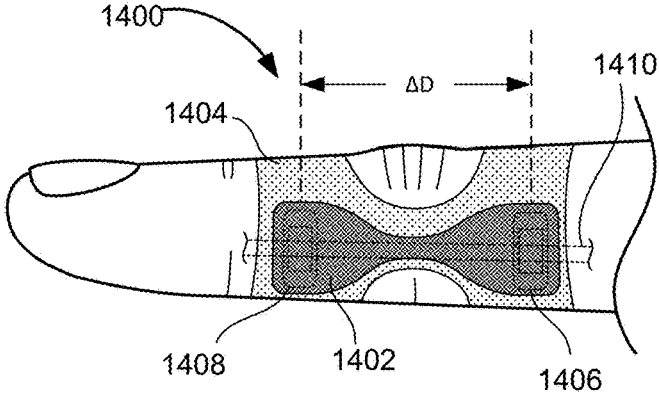
FIG. 14B shows an example ambulatory monitoring device designed to be worn on a finger according to some implementations.

FIG. 14B shows an example ambulatory monitoring device 1400 designed to be worn on a finger according to some implementations. The first and the second arterial distension sensors 1406 and 1408 may, in some instances, each include an instance of the ultrasonic receiver 302 and a portion of the light source system 304 that are described above with reference to FIG. 3.

In some other implementations, the ambulatory monitoring devices disclosed herein can be positioned on a region of interest of the user without the use of a strap or band. For example, the first and the second arterial distension sensors 1406 and 1408 and other components of the monitoring device can be enclosed in a housing that is secured to the skin of a region of interest of the user using an adhesive or other suitable attachment mechanism (an example of a "patch" monitoring device).

Figure 14C:
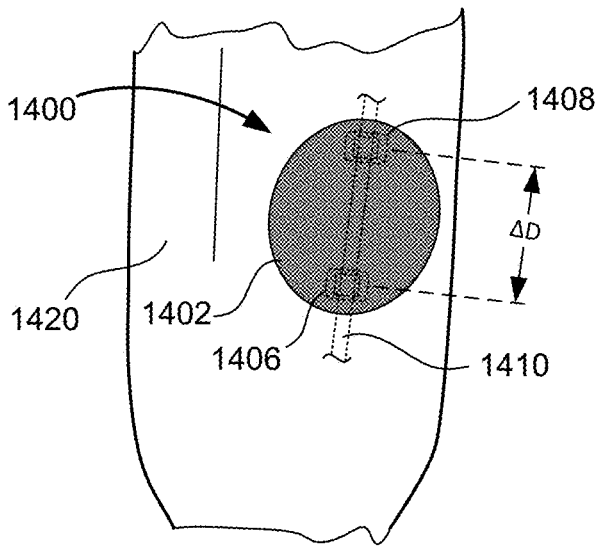
FIG. 14C shows an example ambulatory monitoring device designed to reside on an earbud according to some implementations.

FIG. 14C shows an example ambulatory monitoring device 1400 designed to reside on an earbud according to some implementations. According to this example, the ambulatory monitoring device 1400 is coupled to the housing of an earbud 1420. The first and second arterial distension sensors 1406 and 1408 may, in some instances, each include an instance of the ultrasonic receiver 302 and a portion of the light source system 304 that are described above with reference to FIG. 3.

Implementation examples are described in the following numbered clauses:

1. An apparatus, including: a light source system configured for providing light to a target object on an outer surface of the apparatus, the light source system including a light-steering system including at least a first light-steering device configured to direct light emitted by at least a first light source of the light source system to a first plurality of areas of the target object; an ultrasonic receiver system configured to receive ultrasonic waves generated by the target object responsive to the light from the light source system and to generate ultrasonic receiver signals based, at least in part, on the ultrasonic waves generated by the target object; and a control system configured to: receive the ultrasonic receiver signals from the ultrasonic receiver system, the ultrasonic receiver signals corresponding to each area of the first plurality of areas of the target object; determine a selected area of the target object corresponding to an area from which additional ultrasonic receiver signals will be obtained, where determining the selected area involves detecting a blood vessel within the target object; and control the light source system to obtain the additional ultrasonic receiver signals from the selected area.

2. The apparatus of clause 1, where the light-steering system includes one or more adjustable micromirrors, one or more adjustable lenses, one or more adjustable diffraction gratings, or combinations thereof.

3. The apparatus of clause 1 or clause 2, where determining the selected area involves estimating a signal-to-noise ratio (SNR) of ultrasonic receiver signals corresponding to at least a portion of the blood vessel.

4. The apparatus of clause 3, where determining the selected area involves selecting an area corresponding to a highest SNR.

5. The apparatus of any one of clauses 1-4, where determining the selected area involves selecting an area corresponding to a greatest estimated distance between a first blood vessel wall and a second blood vessel wall.

6. The apparatus of any one of clauses 1-5, where the light-steering system includes a second light-steering device configured to direct light emitted by a second light source of the light source system to a second plurality of areas of the target object.

7. The apparatus of any one of clauses 1-6, where the first light-steering device is configured to direct light emitted by a second light source of the light source system to a second plurality of areas of the target object.

8. The apparatus of any one of clauses 1-7, where the light source system includes a plurality of light guides.

9. The apparatus of clause 8, where the light-steering system is configured to direct light emitted by at least the first light source to each light guide of the plurality of light guides.

10. The apparatus of clause 8 or clause 9, where the ultrasonic receiver system includes a plurality of receiver portions, each receiver portion corresponding to one light guide of the plurality of light guides.

11. The apparatus of any one of clauses 8-10, each light guide of the plurality of light guides is configured to direct a first portion of received light along an axis of the light guide and to direct a second portion of the received light towards the target object.

12. The apparatus of any one of clauses 1-11, where the ultrasonic receiver system includes transparent material and where the light source system is configured for providing light through the transparent material to the target object.

13. The apparatus of any one of clauses 1-12, where the control system is further configured to: estimate one or more blood vessel features based, at least in part, on the additional ultrasonic receiver signals; and estimate blood pressure based, at least in part, on the one or more blood vessel features.

14. The apparatus of clause 13, where the one or more blood vessel features include blood vessel diameter, blood vessel distention, volumetric flow, pulse wave velocity, blood vessel wall thickness, or combinations thereof.

15. The apparatus of any one of clauses 1-14, further including an inertial sensor system including one or more motion detectors, where the control system is further configured to: receive inertial sensor data from the inertial sensor system; determine whether the inertial sensor data indicates apparatus motion that exceeds a threshold; and control the light-steering system according to whether the apparatus motion exceeds the threshold.

16. The apparatus of clause 15, where the control system is further configured to control the light-steering system to compensate for the apparatus motion.

17. The apparatus of clause 15 or clause 16, where the one or more motion detectors include one or more accelerometers.

18. The apparatus of any one of clauses 1-17, where the ultrasonic receiver system includes an array of ultrasonic receiver elements and where the control system is configured to receive ultrasonic receiver signals from each of a plurality of ultrasonic receiver elements in the array.

19. The apparatus of clause 18, where the array of ultrasonic receiver elements includes a two-dimensional array of ultrasonic receiver elements.

20. The apparatus of clause 18 or clause 19, where the array of ultrasonic receiver elements includes an array of electrodes arranged on a piezoelectric layer.

21. The apparatus of clause 20, where the piezoelectric layer includes lead zirconate titanate (PZT) or a piezoelectric composite.

22. The apparatus of any one of clauses 18-21, where the control system is configured to apply a receiver-side beamforming process to the ultrasonic receiver signals, to produce a beamformed ultrasonic receiver image.

23. The apparatus of clause 22, where the receiver-side beamforming process includes a delay-and-sum beamforming process.

24. The apparatus of any one of clauses 1-23, where the apparatus is configured to be worn by, or attached to, a person.

25. An apparatus, including: a light source system configured for providing light to a target object on an outer surface of the apparatus, the light source system including a light-steering system including at least a first light-steering device configured to direct light emitted by at least a first light source of the light source system to a first plurality of areas of the target object; an ultrasonic receiver system configured to receive ultrasonic waves generated by the target object responsive to the light from the light source system and to generate ultrasonic receiver signals based, at least in part, on the ultrasonic waves generated by the target object; and control means for: receiving the ultrasonic receiver signals from the ultrasonic receiver system, the ultrasonic receiver signals corresponding to each area of the first plurality of areas of the target object; determining a selected area of the target object corresponding to an area from which additional ultrasonic receiver signals will be obtained, where determining the selected area involves detecting a blood vessel within the target object; and controlling the light source system to obtain the additional ultrasonic receiver signals from the selected area.

26. The apparatus of clause 25, where the light-steering system includes one or more adjustable micromirrors, one or more adjustable lenses, one or more adjustable diffraction gratings, or combinations thereof.

27. A method, including: controlling a light-steering system to direct light emitted by at least a first light source of a light source system to a first plurality of areas of a target object, where controlling the light-steering system involves controlling one or more adjustable micromirrors, one or more adjustable lenses, one or more adjustable diffraction gratings, or combinations thereof; receiving ultrasonic receiver signals from an ultrasonic receiver system, the ultrasonic receiver signals corresponding to photoacoustic responses of the target object to light provided the light source system to each area of the first plurality of areas; determining a selected area of the target object corresponding to an area from which additional ultrasonic receiver signals will be obtained, where determining the selected area involves detecting a blood vessel within the target object; and controlling the light source system to obtain the additional ultrasonic receiver signals from the selected area.

28. The method of clause 27, where determining the selected area involves estimating a signal-to-noise ratio (SNR) of ultrasonic receiver signals corresponding to at least a portion of the blood vessel and selecting an area corresponding to a highest SNR.

29. The method of clause 27 or clause 28, further including controlling the light-steering system to direct light emitted by a second light source of the light source system to a second plurality of areas of the target object.

30. The method of any one of clauses 27-29, where controlling the light-steering system involves directing light emitted by at least the first light source to each light guide of a plurality of light guides.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also may be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module which may reside on a computer-readable medium. Computer-readable media include both computer storage media and communication media including any medium that may be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those having ordinary skill in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "exemplary" is used exclusively herein, if at all, to mean "serving as an example, instance, or illustration." Any implementation described herein as "exemplary" is not necessarily to be construed as preferred or advantageous over other implementations.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

It will be understood that unless features in any of the particular described implementations are expressly identified as incompatible with one another or the surrounding context implies that they are mutually exclusive and not readily combinable in a complementary and/or supportive sense, the totality of this disclosure contemplates and envisions that specific features of those complementary implementations may be selectively combined to provide one or more comprehensive, but slightly different, technical solutions. It will therefore be further appreciated that the above description has been given by way of example only and that modifications in detail may be made within the scope of this disclosure.

Various modifications to the implementations described in this disclosure may be readily apparent to those skilled in the art, and the generic principles defined herein may be applied to other implementations without departing from the spirit or scope of this disclosure. Thus, the following claims are not intended to be limited to the implementations shown herein, but are to be accorded the widest scope consistent with this disclosure, the principles and the novel features disclosed herein.

Additionally, certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. Moreover, various ones of the described and illustrated operations can itself include and collectively refer to a number of sub-operations. For example, each of the operations described above can itself involve the execution of a process or algorithm. Furthermore, various ones of the described and illustrated operations can be combined or performed in parallel in some implementations. Similarly, the separation of various system components in the implementations described above should not be understood as requiring such separation in all implementations. As such, other implementations are within the scope of the following claims. In some cases, the actions recited in the claims can be performed in a different order and still achieve desirable results.

What is claimed is:

1. An apparatus, comprising:
a light source system configured for providing light to a target object on an outer surface of the apparatus, the light source system including a light-steering system comprising at least a first light-steering device including one or more moveable components, the first light-steering device being configured to direct light emitted by at least a first light source of the light source system to a first plurality of areas of the target object, the first plurality of areas corresponding to a first plurality of positions of the one or more moveable components of the first light-steering device;
an ultrasonic receiver system configured to receive ultrasonic waves generated by the target object responsive to the light from the light source system and to generate ultrasonic receiver signals based, at least in part, on the ultrasonic waves generated by the target object; and
a control system including one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof, the control system being configured to:
receive the ultrasonic receiver signals from the ultrasonic receiver system, the ultrasonic receiver signals corresponding to each area of the first plurality of areas of the target object;
determine a selected area of the target object corresponding to an area from which additional ultrasonic receiver signals will be obtained, wherein determining the selected area involves detecting a blood vessel within the target object and estimating a signal-to-noise ratio (SNR) of ultrasonic receiver signals corresponding to at least a portion of the blood vessel; and
control the light source system to obtain the additional ultrasonic receiver signals from the selected area by positioning the one or more moveable components of the first light-steering device by selecting an area corresponding to a highest estimated SNR of the ultrasonic receiver signals corresponding to at least the portion of the blood vessel.

2. The apparatus of claim 1, wherein the light-steering system includes one or more adjustable micromirrors, one or more adjustable lenses, one or more adjustable diffraction gratings, or combinations thereof.

3. The apparatus of claim 1, wherein determining the selected area involves selecting an area corresponding to a greatest estimated distance between a first blood vessel wall and a second blood vessel wall of the blood vessel.

4. The apparatus of claim 1, wherein the light-steering system includes a second light-steering device configured to direct light emitted by a second light source of the light source system to a second plurality of areas of the target object.

5. The apparatus of claim 1, wherein the first light-steering device is configured to direct light emitted by a second light source of the light source system to a second plurality of areas of the target object.

6. The apparatus of claim 1, wherein the light source system includes a plurality of light guides.

7. The apparatus of claim 6, wherein the light-steering system is configured to direct light emitted by at least the first light source to each light guide of the plurality of light guides.

8. The apparatus of claim 6, wherein the ultrasonic receiver system includes a plurality of receiver portions, each receiver portion corresponding to one light guide of the plurality of light guides.

9. The apparatus of claim 6, each light guide of the plurality of light guides is configured to direct a first portion of received light along an axis of the light guide and to direct a second portion of the received light towards the target object.

10. The apparatus of claim 1, wherein the ultrasonic receiver system includes transparent material and wherein the light source system is configured for providing light through the transparent material to the target object.

11. The apparatus of claim 1, wherein the control system is further configured to:

estimate one or more blood vessel features based, at least in part, on the additional ultrasonic receiver signals; and estimate blood pressure based, at least in part, on the one or more blood vessel features.

12. The apparatus of claim 11, wherein the one or more blood vessel features include blood vessel diameter, blood vessel distention, volumetric flow, pulse wave velocity, blood vessel wall thickness, or combinations thereof.

13. The apparatus of claim 1, further comprising an inertial sensor system including one or more motion detectors, wherein the control system is further configured to:

receive inertial sensor data from the inertial sensor system;

determine whether the inertial sensor data indicates apparatus motion that exceeds a threshold; and control the light-steering system according to whether the apparatus motion exceeds the threshold.

14. The apparatus of claim 13, wherein the control system is further configured to control the light-steering system to compensate for the apparatus motion.

15. The apparatus of claim 13, wherein the one or more motion detectors include one or more accelerometers.

16. The apparatus of claim 1, wherein the ultrasonic receiver system includes an array of ultrasonic receiver elements and wherein the control system is configured to receive ultrasonic receiver signals from each of a plurality of ultrasonic receiver elements in the array.

17. The apparatus of claim 16, wherein the array of ultrasonic receiver elements comprises a two-dimensional array of ultrasonic receiver elements.

18. The apparatus of claim 16, wherein the array of ultrasonic receiver elements comprises an array of electrodes arranged on a piezoelectric layer.

19. The apparatus of claim 18, wherein the piezoelectric layer comprises lead zirconate titanate (PZT) or a piezoelectric composite.

20. The apparatus of claim 16, wherein the control system is configured to apply a receiver-side beamforming process to the ultrasonic receiver signals, to produce a beamformed ultrasonic receiver image.

21. The apparatus of claim 20, wherein the receiver-side beamforming process comprises a delay-and-sum beamforming process.

22. The apparatus of claim 1, wherein the apparatus is configured to be worn by, or attached to, a person.

23. An apparatus, comprising:

a light source system configured for providing light to a target object on an outer surface of the apparatus, the light source system including a light-steering system comprising at least a first light-steering device including one or more moveable components, the first light-steering device being configured to direct light emitted by at least a first light source of the light source system to a first plurality of areas of the target object, the first plurality of areas corresponding to a first plurality of positions of the one or more moveable components of the first light-steering device;

an ultrasonic receiver system configured to receive ultrasonic waves generated by the target object responsive to the light from the light source system and to generate ultrasonic receiver signals based, at least in part, on the ultrasonic waves generated by the target object; and a control system including one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof, the control system being configured for:

receiving the ultrasonic receiver signals from the ultrasonic receiver system, the ultrasonic receiver signals corresponding to each area of the first plurality of areas of the target object;

determining a selected area of the target object corresponding to an area from which additional ultrasonic receiver signals will be obtained, wherein determining the selected area involves detecting a blood vessel within the target object and selecting an area corresponding to a greatest estimated distance between a first blood vessel wall and a second blood vessel wall of the blood vessel; and controlling the light source system to obtain the additional ultrasonic receiver signals from the selected area by positioning the one or more moveable components of the first light-steering device to direct light to the area corresponding to the greatest estimated distance between the first blood vessel wall and the second blood vessel wall.

24. The apparatus of claim 23, wherein the light-steering system includes one or more adjustable micromirrors, one or more adjustable lenses, one or more adjustable diffraction gratings, or combinations thereof.

\* \* \* \* \*